(12) United States Patent
Sill et al.

(10) Patent No.: US 11,891,482 B2
(45) Date of Patent: *Feb. 6, 2024

(54) POLYMER EXCIPIENTS FOR DRUG DELIVERY APPLICATIONS

(71) Applicant: TYNDALL FORMULATION SERVICES, LLC, Tampa, FL (US)

(72) Inventors: Kevin N. Sill, Tampa, FL (US); Bradford T. Sullivan, Clearwater, FL (US)

(73) Assignee: TYNDALL FORMULATION SERVICES, LLC, Tampa, FL (US)

(*) Notice: Subject to any disclaimer, the term of this patent is extended or adjusted under 35 U.S.C. 154(b) by 60 days.

This patent is subject to a terminal disclaimer.

(21) Appl. No.: 17/672,341

(22) Filed: Feb. 15, 2022

(65) Prior Publication Data

US 2022/0251296 A1    Aug. 11, 2022

Related U.S. Application Data

(62) Division of application No. 16/740,195, filed on Jan. 10, 2020, now Pat. No. 11,286,344.

(51) Int. Cl.
| | |
|---|---|
| *A61K 9/19* | (2006.01) |
| *A61K 9/16* | (2006.01) |
| *A61K 31/4738* | (2006.01) |
| *A61K 31/337* | (2006.01) |
| *C08G 69/10* | (2006.01) |

(52) U.S. Cl.
CPC ............ *C08G 69/10* (2013.01); *A61K 9/1641* (2013.01); *A61K 9/19* (2013.01); *A61K 31/337* (2013.01); *A61K 31/4738* (2013.01)

(58) Field of Classification Search
None
See application file for complete search history.

(56) References Cited

U.S. PATENT DOCUMENTS

| | | | |
|---|---|---|---|
| 2,671,772 | A | 3/1954 | MacDonald |
| 7,799,339 | B2 | 9/2010 | Sill et al. |
| 8,980,326 | B2 | 3/2015 | Sill et al. |
| 9,078,930 | B2 | 7/2015 | Sill et al. |
| 10,836,869 | B1 | 11/2020 | Sill et al. |
| 10,918,619 | B1 | 2/2021 | Sill et al. |
| 2008/0274173 | A1 | 11/2008 | Sill |
| 2016/0120985 | A1 | 5/2016 | Matsutani et al. |
| 2018/0028796 | A1 | 8/2018 | Sill |
| 2018/0228796 | A1 | 8/2018 | Sill et al. |

FOREIGN PATENT DOCUMENTS

| | | |
|---|---|---|
| EP | 2660255 | 11/2013 |
| EP | 3266456 | 1/2018 |
| WO | 2002058622 | 8/2002 |
| WO | WO2004017940 | 3/2004 |
| WO | WO2005117833 | 12/2005 |
| WO | WO2008134731 | 11/2008 |

OTHER PUBLICATIONS

Birke et al. (Polysarcosine-containing copolymers: synthesis, characterization, self-assembly, and applications, Progress in Polymer Science, 21 (2018); 163-208). (Year: 2018).*
Adams, et.al. "Amphiphilic Block Copolymers for Drug Delivery" Journal of Pharmaceutical Sciences, 92(7)1343-1355(2003).
Armstrong, "The occurrence, induction, specificity and potential effect of antibodies against poly(ethylene glycol)," PEGylated Protein Drugs: Basic Science and Clinical Applications, Birkhäuser Verlag/Switzerland, pp. 147-168 (2009) (22 pages).
Arnould, et al., "Meganuclease fusion proteins and their use in targeted integration of transforming DNA," Caplus: 2003: 757845 (2020) (2 pages).
Birke, et al., "Polypeptoid-block-polypeptide Copolymers: Synthesis, Characterization, and Application of Amphiphilic Block Copolypept(o)ides in Drug Formulations and Miniemulsion Techniques," Biomacromolecules, 15(2):548-557 (2014).
Birke, et al., "Polysarcosine-containing copolymers: Synthesis, characterization, self-assembly, and applications," Progress in Polymer Science, 81:163-208 (2018).
Chan, et al., "Polypeptoid polymers: Synthesis, characterization, and properties," Biopolymers, 109(1):e23070 (2018).
Chen, et al., "Gold Nanoparticles Coated With Polysarcosine Brushes to Enhance Their Colloidal Stability and Circulation Time in Vivo," Journal of Colloid and Interface Science, 483:201-210 (2016).
Fetsch, et al., "Polypeptoids from N-Substituted Glycine N-Carboxyanhydrides: Hydrophilic, Hydrophobic, and Amphiphilic Polymers with Poisson Distribution," Macromolecules, 44:6746-6758 (2011).
Ford, et al., Nucleic acids and their encoded polypeptides from human bone marrow, Caplus, 2001:661557:(2020).
Fournier, et al. "A Novel One-Step Drug-Loading Procedure for Water-Soluble Amphiphilic Nanocarriers," Pharmaceutical Research, 21(6):962-968 (2004).
Heusmann, "A head-to-head comparison of poly(sarcosine) and poly(ethyleneglycol) in peptidic, amphiphilic block copolymers" Polymer 67:240e248 (2015).
Hu, et al., "Polysarcosine as an Alternative to PEG for Therapeutic Protein Conjugation," Bioconjugate Chemistry, 29(7):2232-2238 (2018).
Keck, et al., "Computer method and apparatus for classifying objects such as protein sequences and its application with cyclic peptides osteogenic modulators of bone morphogenetic protine-7," Caplus 2004: 485563 (2020) (2 pages).
Rios-Doria, et al., "A Versatile Polymer Micelle Drug Delivery System for Encapsulation and In Vivo Stabilization of Hydrophobic Anticancer Drugs," Journal of Drug Delivery 2012: 1-8 (2012).

(Continued)

*Primary Examiner* — Melissa S Mercier
(74) *Attorney, Agent, or Firm* — HALEY GUILIANO LLP; James F. Haley, Jr.; Stacey W. Chung

(57) ABSTRACT

The present disclosure relates to the field of polymer chemistry and more particularly to multiblock copolymers comprising a poly(sarcosine) block and a D,L-mixed poly(amino acid) block and uses thereof.

18 Claims, 1 Drawing Sheet

(56) References Cited

OTHER PUBLICATIONS

Sill, et al., "Synthesis and Characterization of Micelle-Forming PEG-Poly(Amino Acid) Copolymers With Iron-Hydroxamate Cross-Linkable Blocks for Encapsulation and Release of Hydrophobic Drugs," Biomacromolecules, 18(6):1874-1884 (2017).
Varlas, et al., "Poly(sarcosine)-Based Nano-Objects with Multi-Protease Resistance by Aqueous Photoinitiated Polymerization-Induced Self-Assembly" Biomacromolecules, 19(11):4453-4462 (2018).
Viricel, et al., "Monodisperse polysarcosine-based highly-loaded antibody-drug conjugates" Chemical Science, 10(14):4048-4053 (2019).
Weber, et al., "Polysarcosine-Based Lipids: From Lipopolypeptoid Micelles to Stealth-Like Lipids in Langmuir Blodgett Monolayers," Polymers, 8(12):427 (2016) (14 pages).
Weber, et al., "Solution Properties of Polysarcosine: From Absolute and Relative Molar Mass Determinations to Complement Activation" Macromolecules, 51:2653-2661 (2018).
U.S. Appl. No. 16/740,183, filed Jan. 10, 2020, Issued, U.S. Pat. No. 10,836,869.
U.S. Appl. No. 16/740,211, filed Jan. 10, 2020, Issued, U.S. Pat. No. 10,918,619.
U.S. Appl. No. 16/740,195, filed Jan. 10, 2020, Allowed.
U.S. Appl. No. 17/142,757, filed Jan. 6, 2021, Pending.
Hamaguchi, et al., "NK. 105, a Paclitaxel-Incorporating Micellar Nanoparticle Formulation, Can Extend in Vivo Antitumour Activity and Reduce the Neurotoxicity of Paclitaxel," British Journal of Cancer, 92:1240-1246 (2005).
Heller, et al., "The Influence of Block Ionomer Microstructure on Polyplex Properties: Can Simulations Help to Understand Differences in Transfection Efficiency?," Small, 13:160694 (2017) (9 pages).
Heller, et al.," Introducing Peptoplexes: Polylysine-block-Polysarcosine Based Polyplexes for Transfection of HEK 293T Cells," Macromolecular Bioscience, 14(10): 1380-1395 (2014).
Otter, et al., "Folding induced supramolecular assembly into pH-responsive nanorods with a protein repellent shell," Chemical Communications, 54:401-404 (2018).

* cited by examiner

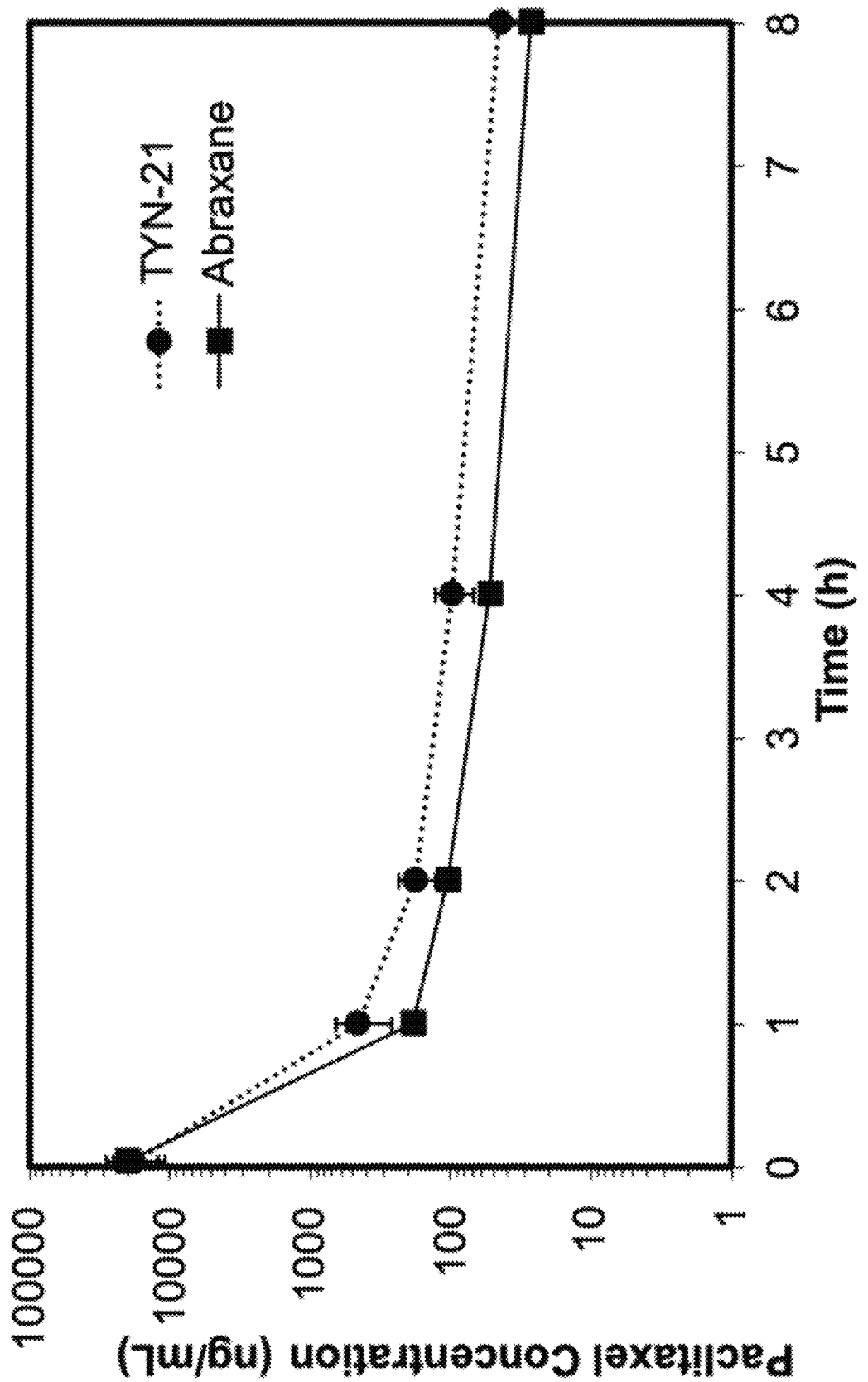

POLYMER EXCIPIENTS FOR DRUG DELIVERY APPLICATIONS

FIELD OF THE DISCLOSURE

This disclosure is directed to the field of polymer chemistry and more particularly to multiblock poly(amino acid) copolymers and uses thereof.

BACKGROUND OF THE DISCLOSURE

Polymer excipients are commonly utilized in the formulation of pharmaceutically active ingredients (APIs). These polymers are used to aid the dissolution of a tablet, to provide a binder, or to modify the viscosity of an oral formulation. In some cases, polymer excipients are used to increase the water solubility of hydrophobic APIs. Poly (ethylene glycol) (PEG), poly(lactic acid) (PLA), poly (lactic acid-co-glycolic acid) (PGLA), and cyclodextrins (CD) are non-limiting examples of polymer excipients that are routinely used in pharmaceutical drug development to improve the solubility of hydrophobic APIs. However, few options remain when these compendial excipients do not adequately solubilize the hydrophobic drug. In such cases, the API can be chemically modified to increase its solubility in water (e.g. prodrug or creation of new API such as a polymer-drug conjugate), the compound can be abandoned, or a new non-compendial excipient can be developed. Often, these new excipients are custom designed for the API of interest. This is evidenced by many drug delivery technologies developed by academic groups that solubilize specific APIs. Unless the new drug product advances to the commercial stage, the public knows little about the synthesis, toxicity, and utility of these solubility-enhancing excipients.

Accordingly, and without wishing to be bound to any particular theory, it would be desirable to develop a polymer excipient that has broad utility to solubilize a wide range of hydrophobic APIs. Such excipient would need to encapsulate amorphous, high-log P compounds (colloquially referred to as "grease balls") as well as highly crystalline hydrophobic APIs (colloquially referred to as "brick dust").

Polymer micelles represent one method for solubilizing hydrophobic compounds. Polymer micelles are formed by the thermodynamic self-assembly of amphiphilic block copolymers into a core-shell type structure (see: Yu, K. et al. *Macromolecules* 1996, 29(19), 6359; Rösler, A. et al. *Adv. Drug Deliv. Rev.* 2012, 64, 270). For a polymer micelle in an aqueous solution, the hydrophilic block of the polymer forms the corona of the micelle, while the hydrophobic block forms the core. If the micelle formation is performed in the presence of an additional hydrophobic molecule (e.g. a hydrophobic drug), then the hydrophobic compound will be spontaneously directed to and sequestered in the hydrophobic core of the polymer micelle. The hydrophobic drug is rendered water-soluble by the hydrophilic corona of the polymer micelle. It is important to note that in this particular application, the drug is physically entrapped and not chemically bound to the polymer chain.

A large number of amphiphilic block copolymers for drug delivery applications have been reported in the literature (see: Kedar, U. et al. *Nanomedicine* 2010, 6(6), 714; Ahmad, Z. et al. *RSC Adv.* 2014, 33, 17028; Kataoka, K. et al. *Adv. Drug Delivery Rev.* 2001, 47(1), 113). PEG-PGLA, PEG-PLA, PEG-poly(amino acid)s, poly(acrylate)-block-poly (methacrylate) and derivatives thereof are all common polymers that have been investigated for polymer micelle based drug delivery applications. A large majority of these polymers include the use of PEG as the hydrophilic component. PEG is widely regarded as a non-toxic, non-immunogenic compound with decades of use in food, cosmetic, and pharmaceutical products. However, recent studies have begun to indicate that there may be an immunogenic response to PEG containing materials, especially with regard to intravenous products (see: Garay, R. et al., *Expert Opin. Drug Delivery*, 2012, 1319-1323; Yang, Q. et al., *Anal. Chem.* 2016, 88(23), 11804-11812; Wenande, E. et al., *Clin. Exp. Allergy*, 2016, 46(7), 907-922; Webster, R *Drug Metab. Dispos,* 2007, 35(1), 9-16). Such PEG containing pharmaceutic products can also produce infusion related reactions (see: Browne, E. K. et al. *J. Pediatr Oncolo. Nurs.* 2018, 35(2), 103). Furthermore, the manufacture of high purity, pharmaceutically acceptable PEG derivatives involves the extremely hazardous polymerization of ethylene oxide and even trace impurities in the product can have significant effects on their applications (see: Vojkovsky, T. et al. *Polymer,* 2016, 105, 72-78; Sill, K. et al. *Biomacromolecules* 2017, 18(6), 1874-1884). This can make utilization of PEG-containing pharmaceuticals expensive, and thus cost-prohibitive for certain applications.

Other polymers commonly used for drug delivery applications are based upon acrylate or other vinyl polymer chemistries. Such polymers are prepared by the anionic or radical polymerization of vinyl monomers. Often, these monomers, such as butyl acrylate, are strong sensitizing agents. Further, these polymers, while biocompatible, do not degrade in vivo because the polymer backbone chain is composed exclusively of carbon-carbon bonds.

BRIEF SUMMARY OF THE DISCLOSURE

The present disclosure is directed to multiblock copolymers comprising a hydrophilic poly(sarcosine) block and a hydrophobic poly(amino acid) block comprising a mixture of D- and L-amino acids. The multiblock copolymers may be synthesized by the polymerization of the corresponding amino acid N-carboxyanhydrides. As described herein, the multiblock copolymers are useful for the encapsulation of hydrophobic molecules, which increases the solubility of the molecule in aqueous solutions. Compositions of the present disclosure include drug products comprising a multiblock copolymer and a hydrophobic drug. Such compositions increase the solubility of said hydrophobic drug in diluents commonly used for parenteral administration. Also provided herein are methods of preparing a composition or unit dose form described herein.

BRIEF DESCRIPTION OF THE DRAWINGS

The drawing depicts the Rat Pharmacokinetic profile of TYN-21 versus Abraxane at equivalent paclitaxel dose of 5.0 mg/kg

DETAILED DESCRIPTION OF CERTAIN EMBODIMENTS OF THE DISCLOSURE

1. General Description

As described herein, the present disclosure is directed to multiblock poly(amino acid) copolymers. The first block is a hydrophilic poly(sarcosine) block and the second is a hydrophobic poly(amino acid) block comprising a mixture of D- and L-amino acids. Such copolymers can spontaneously self-assemble into micellular structures in aqueous solutions with the hydrophilic poly(sarcosine) block forming the corona and the hydrophobic poly(amino acid) block forming the core of the micelle. If a hydrophobic molecule (e.g., an API, compound, drug, or a pharmaceutically active agent) is present during this assembly, it can sequester in the hydrophobic portion of the micelle. This will have the effect of increasing the solubility of the hydrophobic molecule in aqueous solutions. The amide backbone of a poly(sarcosine) block can adopt both cis and trans configurations, while a poly(amino acid) block comprising a mixture of both D- and L-amino acids will disrupt the formation of secondary and tertiary structures. Without wishing to be bound to any particular theory, it is believed that these two properties, taken together, increase the rotational degrees of freedom, which allows the multiblock poly(amino acid) copolymer to assume many conformations which promotes an associated hydrophobic molecule to find the lowest possible energy state. It will be appreciated that if the hydrophobic molecule is a hydrophobic drug, compositions of the present disclosure will be useful for parenteral administration using common aqueous diluents (e.g. saline or D5W) without the need for additional solubilizing agents, such as Cremophor® EL (polyoxyethylated castor oil). One of ordinary skill in the art will recognize the advantage of eliminating the need for Cremophor EL as it is known to cause several infusion-related side effects, including bronchospasm, hypotension, peripheral neuropathy, and anaphylactic reactions. These side effects necessitate pre-medication with $H_1$ and $H_2$ antagonists and prolonged infusion times to reduce the hypersensitivity reactions for Cremophor EL based paclitaxel formulations (see: Authier, N. et al., *Neurotox. Res.* 2001, 3, 301-306; Gelderblom, H. et al., *Eur. J. Cancer* 2001, 37, 1590-1598; Brat, D. et al., *Pharmacology Exp. Ther.* 1992, 261, 803-810; Windebank, A. J. et al., *J. Pharmacology Exp. Ther.* 1994, 268, 1051-1056; Van Zuylen, L. et al., *Investigational New Drugs*, 2001, 19, 125-141. Cremophor EL is also not compatible with standard intravenous tubing as it extracts the plasticizer DEHP (di(2-ethylhexyl)phthalate) from polyvinyl chloride (PVC) materials. Furthermore, drugs formulated with Cremophor EL (e.g. paclitaxel) can become entrapped in Cremophor micelles which results in non-linear pharmacokinetics (see: Sparreboom, A. et al., *Cancer Res*, 1999, 59, 1454-1457).

In some embodiments, the poly(amino acid) copolymers of the present disclosure may be prepared by the polymerization of the corresponding amino acid N-carboxyanhydrides (NCAs). The multiblock copolymers of the disclosure may be prepared by the sequential polymerization of sarcosine NCA followed by a mixture of D- and L-amino acid NCAs. In some embodiments, the polymerization is performed in a single solvent and the final copolymer is isolated via precipitation with a single anti-solvent. The solvents and the reagents are used "as received", with no further steps taken to purify, or to exclude air and/or moisture (e.g. Schlenk techniques), as is commonly employed in NCA polymerizations (see: Aliferis, T. et al. *Biomacromolecules* 2004, 5(5), 1653; Deming, T. J. et al. *Nature* 1997, 390 (6658), 386; Kricheldorf, H. R. α-Amino acid-N-carboxyanhydrides and related heterocycles: syntheses, properties, peptide synthesis, polymerization, Berlin, Springer-Verlag, 2011). It will be appreciated that this will minimize the cost associated with preparing a poly(amino acid) copolymer, especially on commercial scale under Good Manufacturing Practice (GMP) guidance, as a minimal number of solvents will need to be sourced, and quantified during release testing.

2. Definitions

The following are definitions of various terms used herein to describe the present disclosure and are further illustrated by the embodiments, sub-embodiments, and species disclosed herein. These definitions apply to the terms as they are used throughout this specification unless otherwise indicated in specific instances, either individually or as part of a larger group.

For purposes of this disclosure, the chemical elements are identified in accordance with the Periodic Table of the Elements, CRC Handbook of Chemistry and Physics, 100th Ed. Additionally, general principles of organic chemistry are described in: Sorrell, T. *Organic Chemistry*, 2nd Ed., Sausalito, University Science Books, 2005; and Smith, M. B. *March's Advanced Organic Chemistry: Reactions, Mechanisms, and Structure*, 7th Ed., New York, J. John Wiley & Sons, 2001, the entire contents of which are hereby incorporated by reference.

The term "about" when referring to a measurable value such as an amount, a temporal duration, and the like, refers to variations of ±20% or in some instances ±10%, or in some instances ±5%, or in some instances ±2%, or in some instances ±1%, or in some instances ±0.1% from the specified value, as such variations are appropriate to perform the present disclosures.

It is understood that the terms "TFS-1", "poly(sarcosine)$_{175}$-block-poly(d-leucine$_{35}$-co-tyrosine$_{25}$)", "PSar$_{175}$-P(dLeu$_{35}$/Tyr$_{25}$)", "poly[Sar$_{175}$]-block-poly-[D-Leu$_{35}$-co-L-Tyr$_{25}$]", and a copolymer having the following structure:

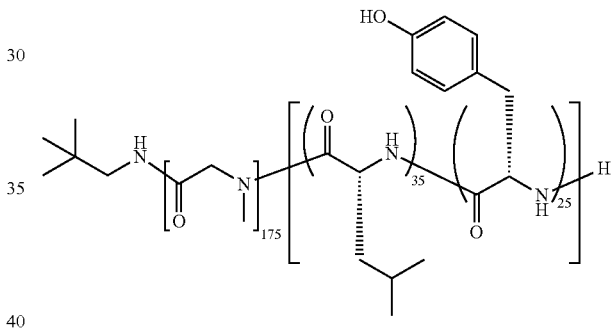

all represent the same compound and can be used interchangeably.

It is understood that the terms "TFS-2", "poly(sarcosine)$_{175}$-block-poly(d-leucine$_{30}$-co-tyrosine$_{20}$)", "PSar$_{175}$-P(dLeu$_{30}$/Tyr$_{20}$)", "poly[Sar$_{175}$]-block-poly-[D-Leu$_{30}$-co-L-Tyr$_{20}$]", and a copolymer having the following structure:

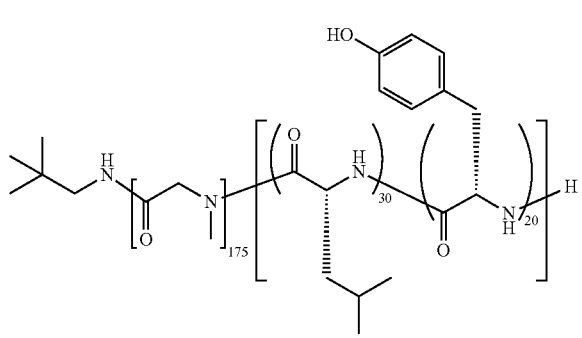

all represent the same compound and can be used interchangeably.

It is understood that the terms "TFS-3", "poly(sarcosine)$_{235}$-block-poly(d-phenylalanine$_{10}$-co-tyrosine$_{30}$)", "PSar$_{235}$-P(dPhe$_{10}$/Tyr$_{30}$)", "poly[Sar$_{235}$]-block-poly-[D-Phe$_{10}$-co-L-Tyr$_{30}$]", and a copolymer having the following structure:

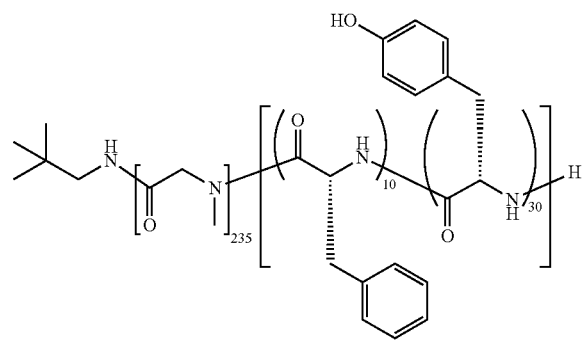

all represent the same compound and can be used interchangeably.

As used herein, the term "block copolymer" refers to a polymer comprising two or more poly(amino acid) portions. As described herein, one or more of the amino acid blocks may be "mixed blocks", meaning that these blocks can contain a mixture of amino acid monomers thereby creating block copolymers of the present disclosure. One skilled in the art will recognize that a monomer repeat unit is defined by parentheses depicted around the repeating monomer unit. The number (or letter representing a numerical range) on the lower right of the parentheses represents the number of monomer units that are present in the polymer chain. In the case where only one monomer represents the block (e.g. a homopolymer), the block will be denoted solely by the parentheses. In the case of a mixed block, multiple monomers comprise a single, continuous block. It will be understood that brackets will define a portion or block. For example, one block may consist of four individual monomers, each defined by their own individual set of parentheses and number of repeat units present. All four sets of parentheses will be enclosed by a set of brackets, denoting that all four of these monomers combine in random, or near random, order to comprise the mixed block. For clarity, the randomly mixed block of [BCADDCBADABCDABC] would be represented in shorthand by [(A)$_4$(B)$_4$(C)$_4$(D)$_4$].

As used herein, the monomer repeat unit described above is a numerical value representing the average number of monomer units comprising the polymer chain. For example, a polymer represented by (A)$_{10}$ corresponds to a polymer consisting of ten "A" monomer units linked together. One of ordinary skill in the art will recognize that the number 10 in this case will represent a distribution of numbers with an average of 10. The breadth of this distribution is represented by the polydispersity index (PDI). A PDI of 1.0 represents a polymer wherein each chain length is exactly the same (e.g. a protein). A PDI of 2.0 represents a polymer wherein the chain lengths have a Gaussian distribution. Polymers of the present disclosure typically possess a PDI of less than 1.20.

As used herein, "multiblock copolymer" or "copolymer" refers to a polymer comprising two or more poly(amino acid) blocks.

As used herein, the term "poly(amino acid)" or "amino acid block" refers to a covalently linked amino acid chain wherein each monomer is an amino acid unit. Such amino acid units include natural and unnatural amino acids. Such poly(amino acids) include those having suitably protected functional groups. For example, amino acid monomers may have hydroxyl or amino moieties, which are optionally protected by a hydroxyl protecting group or an amine protecting group, as appropriate. As used herein, an amino acid block comprises one or more monomers or a set of two or more monomers. In certain embodiments, an amino acid block comprises one or more monomers such that the overall block is hydrophilic or hydrophobic. In still other embodiments, amino acid blocks of the present disclosure include random amino acid blocks, including blocks comprising a mixture of amino acid residues. Exemplary poly(amino acids) include poly(D-leucine-co-tyrosine), and poly(D-phenylalanine-co-tyrosine).

As used herein, the term "D,L-mixed poly(amino acid) block" refers to a poly(amino acid) block wherein the poly(amino acid) consists of a mixture of amino acids in both the D- and L-configurations. In certain embodiments, the D,L-mixed poly(amino acid) block is hydrophobic. In other embodiments, the D,L-mixed poly(amino acid) block consists of a mixture of D-configured hydrophobic amino acids and L-configured hydrophilic amino acid side-chain groups such that the overall poly(amino acid) block comprising is hydrophobic.

As used herein, the phrase "natural amino acid" refers to any amino acid naturally occurring in proteins and those naturally occurring in nature. Such natural amino acids include the nonpolar, or hydrophobic amino acids, glycine, alanine, valine, leucine, isoleucine, methionine, phenylalanine, tryptophan, and proline. Cysteine is sometimes classified as nonpolar or hydrophobic and other times as polar. Natural amino acids also include polar, or hydrophilic amino acids, such as tyrosine, serine, threonine, aspartic acid (also known as aspartate, when charged), glutamic acid (also known as glutamate, when charged), asparagine, and glutamine. Certain polar, or hydrophilic, amino acids have charged side chains. Such charged amino acids include lysine, arginine, and histidine. One of ordinary skill in the art would recognize that protection of a polar or hydrophilic amino acid side chain can render that amino acid nonpolar. For example, a suitably protected tyrosine hydroxyl group can render that tyrosine nonpolar and hydrophobic by virtue of protecting the hydroxyl group. For clarity, sarcosine is an amino acid naturally occurring in nature.

As used herein, the phrase "natural amino acid side chain group" refers to the side-chain group of any natural amino acid, as defined herein. For clarity, the side chain group —CH$_3$ would represent the amino acid alanine, a natural amino acid side chain group.

As used herein, the phrase "unnatural amino acid" refers to any amino acid not included in the list of those amino acids naturally occurring in proteins, and naturally occurring in nature, as described above. Unnatural amino acids also include homoserine, ornithine, and thyroxine. Exemplary unnatural amino acids include β-trityl-asparagine, β-benzyl-aspartate, S-benzyl-cysteine, cyclohexylglycine, γ-benzyl-glutamate, γ-tert-butyl-glutamate, ε-trifluoroacetyl-lysine, ε-Boc-lysine, ε-benzyl-lysine, β-benzyl-serine, O-acetyl-tyrosine. Other unnatural amino acids include modified amino acids, including those that are N-alkylated, cyclized, phosphorylated, acetylated, amidated, azidylated, labelled, and the like.

As used herein, the phrase "unnatural amino acid side chain group" refers to the side-chain group of any unnatural amino acid, as defined herein. For clarity, the side chain group —(CH$_2$)$_2$CO$_2$CH$_2$C$_6$H$_5$ would represent γ-benzyl-glutamate, an unnatural amino acid side chain group.

As used herein, the term "amino acid", is understood to be a generic term and encompassing both natural amino acids and unnatural amino acids. The term "D-amino acid" is understood to refer to a natural or unnatural amino acid with the D-configuration. The term "L-amino acid" is understood to refer to a natural or unnatural amino acid with the L-configuration.

As used herein, the term "tacticity" refers to the stereochemistry of the poly(amino acid) block. A poly(amino acid) block consisting of a single stereoisomer (e.g. all L isomer) is referred to as "isotactic". A poly(amino acid) consisting of a random incorporation of D- and L-amino acid monomers is referred to as an "atactic" polymer. A poly(amino acid) with alternating stereochemistry (e.g. . . . DLDLDL . . . ) is referred to as a "syndiotactic" polymer. Polymer tacticity is described in more detail in: Odian, G. *Principles of Polymerization*, 4th Ed., New York, John Wiley & Sons, 1991, the entire contents of which are hereby incorporated by reference.

As used herein, the phrase "living polymer chain-end" refers to the terminus resulting from a polymerization reaction which maintains the ability to react further with additional monomer or with a polymerization terminator.

As used herein, the term "termination" refers to attaching a terminal group to a polymer chain-end by the reaction of a living polymer with an appropriate compound. Alternatively, the term "termination" may refer to attaching a terminal group to an amine or hydroxyl end, or derivative thereof, of the polymer chain.

As used herein, the term "polymerization terminator" is used interchangeably with the term "polymerization terminating agent" and refers to a compound that reacts with a living polymer chain-end to afford a polymer with a terminal group. Alternatively, the term "polymerization terminator" may refer to a compound that reacts with an amine or hydroxyl end, or derivative thereof, of the polymer chain, to afford a polymer with a terminal group.

As used herein, the term "polymerization initiator" refers to a compound, which reacts with, or whose anion or free base form reacts with, the desired monomer in a manner which results in polymerization of that monomer. In certain embodiments, the polymerization initiator is an amine.

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments aliphatic groups contain 1-4 carbon atoms. The number of carbon atoms present in the aliphatic groups can also be defined prior to recitation of said aliphatic group. For example, the term (C1-C6)aliphatic refers to an aliphatic group as defined herein comprising from 1 to 6 carbon atoms. It is specifically intended that the disclosure includes each and every individual sub combination of the members of such range. In particular, the term (C1-C6)aliphatic is intended to include C1 aliphatic (e.g., methyl), C2 aliphatic (e.g., ethyl, ethylene or ethylyne), C3 aliphatic, C4 aliphatic, C5 aliphatic and C6 aliphatic). Aliphatic groups include, but are not limited to, linear or branched, alkyl, alkenyl, and alkynyl groups, and hybrids thereof such as (cycloalkyl) alkyl, (cycloalkenyl)alkyl or (cycloalkyl)alkenyl.

The term "heteroatom" means one or more of oxygen, sulfur, nitrogen, phosphorus, or silicon. This includes any oxidized form of nitrogen, sulfur, phosphorus, or silicon; the quaternized form of any basic nitrogen, or; a substitutable nitrogen of a heterocyclic ring including =N— as in 3,4-dihydro-2H-pyrrolyl, —NH— as in pyrrolidinyl, or =N(R[†])— as in N-substituted pyrrolidinyl.

The term "unsaturated", as used herein, means that a moiety has one or more units of unsaturation.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains three to seven ring members. The term "aryl" may be used interchangeably with the term "aryl ring".

As described herein, compounds of the disclosure may contain "optionally substituted" moieties. In general, the term "substituted", whether preceded by the term "optionally" or not, means that one or more hydrogens of the designated moiety are replaced with a suitable substituent. In some embodiments, an "optionally substituted" group may have a suitable substituent at each substitutable position of the group, and when more than one position in any given structure may be substituted with more than one substituent selected from a specified group, the substituent may be either the same or different at every position. In some embodiments, an "optionally substituted" group refers to a group having 0-5 substituents independently selected from a specified group. In some embodiments, an "optionally substituted" group refers to a group having 0-3 substituents independently selected from a specified group. Combinations of substituents envisioned by this disclosure are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Monovalent substituents on a substitutable carbon atom of an "optionally substituted" group are independently halogen; —(CH$_2$)$_{0-4}$R°; —(CH$_2$)$_{0-4}$OR°; —O—(CH$_2$)$_{0-4}$C(O) OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S) R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O) N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$ NR°$_2$; —(CH$_2$)$_{0-4}$S(O)R°; —N(R°)S(O)$_2$NR°$_2$; —N(R°)S (O)$_2$R°; —N(OR°)R°; —C(NH)NR°$_2$; —P(O)$_2$R°; —P(O) R°$_2$; —O P(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Monovalent substituents on R° (or the ring formed by taking two independent occurrences of R° together with their intervening atoms), are independently halogen, —$(CH_2)_{0-2}$R$^\bullet$, -(haloR$^\bullet$), —$(CH_2)_{0-2}$OH, —$(CH_2)_{0-2}$OR$^\bullet$, —$(CH_2)_{0-2}$CH(OR$^\bullet$)$_2$; —O(haloR$^\bullet$), —CN, —N$_3$, —$(CH_2)_{0-2}$C(O)R$^\bullet$, —$(CH_2)_{0-2}$C(O)OH, —$(CH_2)_{0-2}$C(O)OR$^\bullet$, —$(CH_2)_{0-2}$SR$^\bullet$, —$(CH_2)_{0-2}$SH, —$(CH_2)_{0-2}$NH$_2$, —$(CH_2)_{0-2}$NHR$^\bullet$, —$(CH_2)_{0-2}$NR$^\bullet_2$, —NO$_2$, —SiR$^\circ_3$, —OSiR$^\circ_3$, —C(O)SR$^\bullet$, —$(C_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from $C_{1-4}$ aliphatic, —$CH_2$Ph, —$O(CH_2)_{0-1}$Ph, or a 5-6-membered saturated, partially unsaturated, or aryl ring having 0-4 heteroatoms independently selected from nitrogen, oxygen, or sulfur. Such divalent substituents on a saturated carbon atom of R° include =O and =S.

Divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. A tetravalent substituent that is bound to vicinal substitutable methylene carbons of an "optionally substituted" group is the dicobalt hexacarbonyl cluster represented by

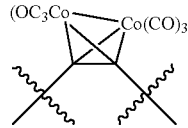

when depicted with the methylenes which bear it.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently $C_{1-4}$ aliphatic, —$CH_2$Ph, —$O(CH_2)_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)N R$^\dagger_2$, —C(NH)NR$^\dagger_2$, or —N(R$^\dagger$)S(O)$_2$R$^\dagger$; wherein each R$^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently $C_{1-4}$ aliphatic, —$CH_2$Ph, —$O(CH_2)_{0-1}$Ph, or a 5-6-membered saturated, partially unsaturated, or aryl ring having 0-4 heteroatoms independently selected from nitrogen, oxygen, or sulfur.

In some embodiments, an "optionally substituted aliphatic" group refers to an aliphatic group as defined above, that is substituted with 0-5 substituents selected from the group consisting of halogen, hydroxy, cyano, nitro, oxo, phenyl, azido, or alkyne wherein said phenyl is substituted with 0-5 substituents selected from halogen, —CH$_3$, —CF$_2$H, —CF$_3$, —OCH$_3$ or —OH. For example, an "optionally substituted aliphatic" group may refer to a methyl group that is substituted with a $C_6H_5$ group, i.e., a benzyl group (—$CH_2C_6H_5$).

In some embodiments, an "optionally substituted aliphatic" group refers to an aliphatic group as defined above, that is substituted with 0-3 substituents selected from the group consisting of halogen, hydroxy, cyano, nitro, oxo, phenyl, azido, or alkyne wherein said phenyl is substituted with 0-3 substituents selected from halogen, —CH$_3$, —CF$_2$H, —CF$_3$, —OCH$_3$ or —OH. For example, an "optionally substituted aliphatic" group may refer to a methyl group that is substituted with a $CH_2C_6H_5$ group, i.e., a benzyl group.

Protected hydroxyl groups are well known in the art and include those described in detail in Wuts, P. G. M. *Protecting Groups in Organic Synthesis,* 5$^{th}$ Ed., New York, John Wiley & Sons, 2014, the entirety of which is incorporated herein by reference. Examples of suitably protected hydroxyl groups further include, but are not limited to, esters, carbonates, sulfonates allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benylbenzoate, 2,4,6-trimethylbenzoate. Examples of carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of silyl ethers include trimethylsilyl, triethylsilyl, t-butyldimethylsilyl, t-butyldiphenylsilyl, triisopropylsilyl ether, and other trialkylsilyl ethers. Examples of alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Wuts (2014). Mono-protected amines further include, but are not limited to, aralkylamines, carbamates, allyl amines, amides, and the like. Examples of mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Di-protected amines include amines that are substituted with two substituents independently selected from those described above as mono-protected amines, and further include cyclic imides, such as phthalimide, maleimide, succinimide, and the like. Di-protected amines also include pyrroles and the like, 2,2,5,5-tetramethyl-[1,2,5]azadisilolidine and the like, and azide.

Protected aldehydes are well known in the art and include those described in detail in Wuts (2014). Protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Wuts (2014). Protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional protected carboxylic acids include oxazolines and ortho esters.

Protected thiols are well known in the art and include those described in detail in Wuts (2014). Protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the disclosure. Unless otherwise stated, all tautomeric forms of the compounds of the disclosure are within the scope of the disclosure. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this disclosure. Such compounds are useful, for example, as in neutron scattering experiments, as analytical tools or probes in biological assays.

As used herein, the term "detectable moiety" is used interchangeably with the term "label" and relates to any moiety capable of being detected (e.g., primary labels and secondary labels). A "detectable moiety" or "label" is the radical of a detectable compound.

"Primary" labels include radioisotope-containing moieties (e.g., moieties that contain $^{32}P$, $^{33}P$, $^{35}S$, or $^{14}C$), mass-tags, and fluorescent labels, and are signal-generating reporter groups which can be detected without further modifications.

"Secondary" labels include moieties such as biotin, or protein antigens, that require the presence of a second compound to produce a detectable signal. For example, in the case of a biotin label, the second compound may include streptavidin-enzyme conjugates. In the case of an antigen label, the second compound may include an antibody-enzyme conjugate. Additionally, certain fluorescent groups can act as secondary labels by transferring energy to another compound or group in a process of nonradiative fluorescent resonance energy transfer (FRET), causing the second compound or group to then generate the signal that is detected.

The terms "fluorescent label", "fluorescent group", "fluorescent compound", "fluorescent dye", and "fluorophore", as used herein, refer to compounds or moieties that absorb light energy at a defined excitation wavelength and emit light energy at a different wavelength. Examples of fluorescent compounds include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethyl-rhodamine (TAMRA), Texas Red, Texas Red-X.

The term "substrate", as used herein refers to any material or macromolecular complex to which a multiblock copolymer can be attached. Examples of commonly used substrates include, but are not limited to, glass surfaces, silica surfaces, plastic surfaces, metal surfaces, surfaces containing a metallic or chemical coating, membranes (e.g., nylon, polysulfone, silica), micro-beads (e.g., latex, polystyrene, or other polymer), porous polymer matrices (e.g., polyacrylamide gel, polysaccharide, polymethacrylate), macromolecular complexes (e.g., protein, polysaccharide).

Unless otherwise indicated, radioisotope-containing moieties are optionally substituted hydrocarbon groups that contain at least one radioisotope. Unless otherwise indicated, radioisotope-containing moieties contain from 1-40 carbon atoms and one radioisotope. In certain embodiments, radioisotope-containing moieties contain from 1-20 carbon atoms and one radioisotope.

The term "isotopic enrichment" or "isotopically enriched" refers to the relative abundance of an isotope being altered, thus producing a form of the element that has been enriched in one particular isotope and depleted in its other isotopic forms. For example, a $C^{14}$ compound is said to have been isotopically enriched.

The term "as received" when referring to the use of a solvent, reagent, resin, or other component used in a chemical reaction or isolation refers to their use in the state provided by the manufacturer without any additional isolation, and/or purification.

As used herein, the term "hydrophobic molecule" refers to a compound, drug, therapeutic agent, or an active pharmaceutical ingredient, and their pharmaceutically acceptable salts.

As used herein, the terms "drug", "therapeutic agent", "pharmaceutical", "medicine" and derivatives thereof, are used interchangeably and refer to a substance intended for use in the diagnosis, cure, mitigation, treatment, or prevention of disease.

As used herein, the terms "drug loaded" and "encapsulated", and derivatives thereof, are used interchangeably. In accordance with the present disclosure, a "drug loaded" micelle refers to a micelle having a drug, or therapeutic agent, situated within the core of the micelle. In certain instances, the drug or therapeutic agent is situated at the interface between the core and the hydrophilic corona. This is also referred to as a drug, or therapeutic agent, being "encapsulated" within the micelle.

As used herein, "weight loading" refers to the ratio of a drug to the total drug product formulation which can include, but is not limited to, drugs, excipients and copolymers. Weight loading is expressed as a weight percentage (% w/w), for example; 20 mg of a drug in a total formulation further comprising 90 mg of a cryoprotectant and 90 mg of a copolymer would be expressed as 10% weight loading, (20/(20+90+90)=10%).

As used herein, "feed ratio" refers to the ratio of drug combined with a copolymer during the manufacturing of a drug product. Feed ratio is expressed as a weight percentage (% w/w), for example; 100 mg of a drug combined with 500 mg of a copolymer (independent of other components) would be expressed as a feed ratio of 20% (100/500=20%).

As used herein, "high shear mix" or "high shear mixing", refers to dispersing a combination of components into a continuous phase which would normally be immiscible via emulsification, sonication, or microfluidizing.

As used herein, "unit dosage form" or "unit dose form" refers to a physically discrete unit of a formulation appropriate for the subject to be treated. It will be understood, however, that the total daily usage of the compositions of the present disclosure will be decided by the attending physician within the scope of sound medical judgement. The specific effective dose level for any particular subject or organism will depend on a variety of factors including the disorder being treated and the severity of the disorder; activity of specific active agent employed; specific composition employed; age, body weight, general health, sex and diet of the subject; time of administration, and rate of excretion of the specific active agent employed; duration of treatment, drugs/and or additional therapies used in combination or coincidental with specific compound(s) employed and like factors well known in the medical arts.

As used herein, a "drug product" means a therapeutic agent, and one or more "excipients" selected from, but not limited to, tonicity agents, cryoprotectants, multiblock copolymers, stabilizing agents, antiadherents, binders, coatings, colors, disintegrants, flavors, glidants, lubricants, preservatives, sorbents, sweeteners, and vehicles. As appreciated by those skilled in the art, the amounts of each excipient will depend on the therapeutic agent, the route of administration, the desired biological endpoint, the target cell or tissue.

As used herein, a "cryoprotectant" or "cryoprotective agent" refers to compounds which either prevent freezing or prevent damage, or alteration to other compounds related to freezing. This includes, but is not limited to: sugars, monosaccharides, disaccharides, polyalcohols, amino acids, glycine, polyvinyl pyrrolidine, polyethylene glycol, mannitol, sorbitol, sucrose, glucose, raffinose, sucralose, lactose, trehalose, dextran, and dextrose.

As used herein, a "therapeutically effective amount" means an amount of a substance (e.g. a therapeutic agent, composition, and/or formulation) that elicits a desired biological response. In some embodiments, a therapeutically effective amount of a substance is an amount that is sufficient, when administered as part of a dosing regimen to a subject suffering from or susceptible to a disease, disorder, and/or condition, to treat, diagnose, slow the progression of and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, slows the progression of delays onset of, reduces severity of and/or reduces incidence of one or more symptoms or features of the disease, disorder, and/or condition. In some embodiments, a "therapeutically effective amount" is at least a minimal amount of a compound, or composition containing a compound, which is sufficient for treating one or more symptoms of a disease or disorder associated with proliferative diseases, such as cancer.

The term "subject", as used herein, means a mammal and includes human and animal subjects, such as domestic animals (e.g. horses, dogs, cats, etc.).

The terms "treat" or "treating," as used herein, refers to partially or completely alleviating, inhibiting, delaying onset of, slowing the progression of, ameliorating and/or relieving a disease or disorder, or one or more symptoms of the disease or disorder. As used herein, the terms "treatment," "treat," and "treating" refer to partially or completely alleviating, inhibiting, delaying onset of, slowing the progression of, ameliorating and/or relieving a disease or disorder, or one or more symptoms of the disease or disorder, as described herein. In some embodiments, treatment may be administered after one or more symptoms have developed. In some embodiments, the term "treating" includes preventing, slowing or halting the progression of a disease or disorder. In other embodiments, treatment may be administered in the absence of symptoms. For example, treatment may be administered to a susceptible individual prior to the onset of symptoms (e.g. in light of a history of symptoms and/or in light of genetic or other susceptibility factors). Treatment may also be continued after symptoms have resolved, for example to prevent or delay their recurrence. Thus, in some embodiments, the term "treating" includes preventing relapse or recurrence of a disease or disorder The term "parenteral" or "parenterally" as used herein includes subcutaneous, intravenous, intramuscular, intra-articular, intra-synovial, intrasternal, intrathecal, intrahepatic, intralesional and intracranial injection or infusion techniques for administration. Preferably, the compositions are administered intraperitoneally or intravenously. Sterile injectable forms of the compositions of this disclosure may be aqueous or oleaginous suspension. These suspensions may be formulated according to techniques known in the art using dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

It is understood that the terms "TYN-21" refers to a formulation of paclitaxel, TFS-2, and trehalose wherein the paclitaxel is about 13%±2% weight loading of the formulation.

It is understood that the terms "TYN-38" refers to a formulation of SN-38, TFS-3, and trehalose wherein the SN-38 is about 10%±2% weight loading of the formulation.

3. Description of Exemplary Embodiments

3.1 Multiblock Copolymers

In some aspects the present disclosure relates to multiblock copolymers comprising a poly(sarcosine) block and a D,L-mixed poly(amino acid) block. In certain embodiments, the disclosure provides a multiblock copolymer of Formula I:

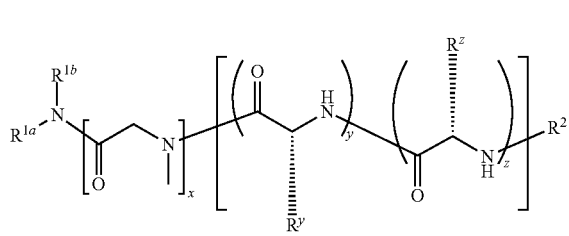

wherein:
$R^{1a}$ is H or an optionally substituted aliphatic group;
$R^{1b}$ is H or an optionally substituted aliphatic group;
$R^2$ is H, an optionally substituted aliphatic group or an optionally substituted CO—(C1-C6)aliphatic group;
each $R^y$ is independently a D-amino acid side chain;
each $R^z$ is independently a L-amino acid side chain;
x is 125-350;
y is 5-35;
z is 5-35.

In some aspects, the present disclosure relates to multiblock copolymers wherein the hydrophilic block comprises a polymer of N-methyl glycine. Those skilled in the art will recognize that other N-alkyl glycines could be used to produce a water-soluble block (see: Robinson, J. W. et al. *Macromolecules* 2013, 46(3), 580). In some embodiments the present disclosure includes multiblock copolymers wherein the hydrophilic block is poly(N-methyl glycine), poly(N-ethyl glycine), poly(N-{n-propyl}) glycine, poly(N-isopropyl) glycine, or poly(N-allyl) glycine. In some aspects, the present disclosure also includes mixtures of two or more N-alkyl glycines used to construct the water-soluble block, such as a mixture of N-methyl glycine and N-ethyl glycine.

In some aspects, the present disclosure relates to multiblock copolymers of Formula I comprising a poly(sarcosine) block initiating from an amine-containing moiety with optionally substituted aliphatic groups represented by $R^{1a}$ and $R^{1b}$. In some embodiments, $R^{1a}$ is a hydrogen and $R^{1b}$ is an optionally substituted aliphatic group. In some embodiments, $R^{1a}$ is an optionally substituted aliphatic group or hydrogen and $R^{1b}$ is an optionally substituted aliphatic group. In some embodiments, the present disclosure envisions substitutions at $R^{1a}$ and $R^{1b}$ which may add functionality to the multiblock copolymer of Formula I which would otherwise not be present, including, but not limited to, a detectable moiety, a fluorescent label, or a substrate. Those skilled in the art will recognize that many substitutions of $R^{1a}$ and $R^{1b}$ are possible. The substitutions of $R^{1a}$ and $R^{1b}$ envisioned by the present disclosure include, but are not limited to, in some embodiments, optionally substituted benzyl groups, optionally substituted hydrocarbons, optionally substituted silyl groups, poly(amino acid) polymers, poly(ethylene glycol) polymers, poly(N-isopropylacrylamide) polymers, poly(acrylamide) polymers, poly(2-oxazoline) polymers, poly(ethylenimine), poly(acrylic acid) polymers, poly(methacrylate) polymers, poly(vinyl alcohol) polymers, poly(vinylpyrrolidone) polymers, and their corresponding amine salts. In some embodiments, the $R^{1a}$ aliphatic group is selected from (C1-C6)alkyl, (C1-C6)alkene, (C1-C6)alkyne or (C3-C10)cycloalkyl, wherein the (C1-C6)alkyl, (C1-C6)alkene, (C1-C6)alkyne or (C3-C10) cycloalkyl are substituted with 0-5 halogen, hydroxy, cyano, nitro, oxo or phenyl, wherein said phenyl is substituted with 0-3 substituents selected from halogen, —CH$_3$, —CF$_2$H, —CF$_3$, —OCH$_3$ or —OH. In some embodiments, the $R^{1b}$ aliphatic group is selected from (C1-C6)alkyl, (C1-C6)alkene, (C1-C6)alkyne or (C3-C10)cycloalkyl, wherein the (C1-C6)alkyl, (C1-C6)alkene, (C1-C6)alkyne or (C3-C10) cycloalkyl are substituted with 0-5 halogen, hydroxy, cyano, nitro, oxo or phenyl groups, wherein said phenyl is substituted with 0-3 substituents selected from halogen, —CH$_3$, —CF$_2$H, —CF$_3$, —OCH$_3$ or —OH. In some embodiments, $R^{1b}$ is selected from a benzyl, methoxybenzyl, neopentyl (i.e., CH$_2$C(CH$_3$)$_3$) or hexyl group). In a preferred embodiment, $R^{1a}$ is H and $R^{1b}$ is neopentyl. In another preferred embodiment, $R^{1a}$ is H and $R^{1b}$ is benzyl. In another preferred embodiment, $R^{1a}$ is H and $R^{1b}$ is p-methylbenzyl. In another preferred embodiment, $R^{1a}$ is H and $R^{1b}$ is p-methoxybenzyl. In another preferred embodiment, $R^{1a}$ is H and $R^{1b}$ is n-hexyl.

In certain embodiments, the present disclosure relates to multiblock copolymers comprising a D,L-mixed poly(amino acid) block comprises amino acids such that the block is hydrophobic overall. As defined above for a composition represented by Formula I, $R^y$ and $R^z$ represent a D- and an L-amino acid respectively. It will be appreciated by one skilled in the art that the D,L-mixed poly(amino acid) block can comprise one or more natural amino acid side-chain group or unnatural amino acid side-chain group that is not generally considered hydrophobic but that the inclusion of an amino acid side-chain group or unnatural amino acid side-chain group which is hydrophobic can make the overall block hydrophobic. For example, in certain circumstances, tyrosine would be considered a hydrophilic amino acid due to its phenol functionality, but a poly(amino acid) block of (tyrosine)$_{20}$-co-(leucine)$_{30}$ is hydrophobic overall, in part, due to the inclusion of a substantial amount of leucine (e.g., an excess of hydrophobic units), a generally considered hydrophobic amino acid in the art. It will also be appreciated that amino acid side chain protecting groups can convert a generally considered hydrophilic amino acid into a generally considered hydrophobic amino acid. For example, glutamic acid is generally considered a hydrophilic amino acid in the art. However, protection of the carboxylate can render the amino acid side chain hydrophobic, as is the case with γ-benzyl-glutamate.

In certain embodiments each $R^y$ is derived from a hydrophilic D-amino acid, and each $R^z$ is derived from a hydrophobic L-amino acid for a composition represented by Formula I.

In certain embodiments each $R^y$ is derived from a hydrophobic D-amino acid, and each $R^z$ is derived from a hydrophilic L-amino acid for a composition represented by Formula I.

In certain embodiments each $R^y$ is derived from a hydrophobic D-amino acid, and each $R^z$ is derived from a hydrophobic L-amino acid for a composition represented by Formula I.

In some embodiments, each $R^y$ is independently the side chain of γ-benzyl-D-glutamate, D-leucine, D-tyrosine, D-phenylalanine, D-alanine, D-valine, D-isoleucine, D-norleucine, O-acetyl-D-tyrosine, O-benzyl-D-tyrosine, or δ-benzyl-D-lysine. In some embodiments, each $R^z$ is independently the side chain of γ-benzyl-L-glutamate, L-leucine, L-tyrosine, L-phenylalanine L-alanine, L-valine, L-isoleucine, L-norleucine, O-acetyl-L-tyrosine, O-benzyl-L-tyrosine, or ε-benzyl-L-lysine. In some embodiments, each $R^y$ is independently the side of D-leucine, D-phenylalanine, or D-tyrosine. In some embodiments, each $R^z$ is independently the side chain of L-leucine, L-phenylalanine, or L-tyrosine.

As described above for a composition represented by Formula I, x and y represent the number of residues for a natural or unnatural D- and an L-amino acid in a poly(amino acid) block respectively. One skilled in the art will recognize the selection of $R^y$ and $R^z$, and the selection of the y and z values, will vary depending on the ultimate role the final multiblock copolymer is to fulfill. It will also be appreciated, for some desired roles, that the length of the sarcosine block, represented by x, is not independent of y and z.

In some aspects, the present disclosure relates to multiblock copolymers of wherein one of the core amino acids, whether it be the D- or the L-amino acid, is replaced by another amino acid that would disrupt the helical structure normally adopted by a isotactic poly(amino acid) polymer. Those amino acids envisioned by the disclosure include, but are not limited to, N-substituted glycines (e.g. sarcosine), proline, and/or glycine.

In some embodiments, the present disclosure relates to multiblock copolymers of Formula I, wherein $R^2$ is selected from H, an optionally substituted aliphatic group, CO—(C1-C6)aliphatic, or —COCH$_3$. The present disclosure envisions substitutions at $R^2$ which may add functionality to the multiblock copolymer of Formula I which would otherwise not be present, including, but not limited to, a detectable moiety, a fluorescent label, or a substrate. In some embodiments, $R^2$ is selected such that an amide bond is formed. In a preferred embodiment, $R^2$ is an acetyl group. In another preferred embodiment, $R^2$ is isotopically enriched. Those skilled in the art will recognize that isotopically enriched materials can be useful probes in biological assays, such as quantitative whole-body autoradiography (QWBA) assays useful for determining the distribution of a composition in an animal.

In certain embodiments, the disclosure provides a multiblock copolymer of Formula I, GC wherein:

$R^{1a}$ is an optionally substituted aliphatic group;

$R^{1b}$ is H;

$R^2$ is H or COCH$_3$;

each $R^y$ is independently a D-amino acid side chain;

each $R^z$ is independently a L-amino acid side chain;

x is 125-350;

y is 5-35;

z is 5-35.

In certain embodiments, the disclosure provides a multiblock copolymer of Formula I, GC wherein:

$R^{1a}$ is an optionally substituted aliphatic group;

$R^{1b}$ is H;

$R^2$ is H or COCH$_3$;

each $R^y$ is an amino acid side chain corresponding to that of D-leucine;

each $R^z$ is an amino acid side chain corresponding to that of L-tyrosine;

x is 125-350;

y is 5-35;

z is 5-35.

One embodiment of the disclosure provides a multiblock copolymer represented by the following structure:

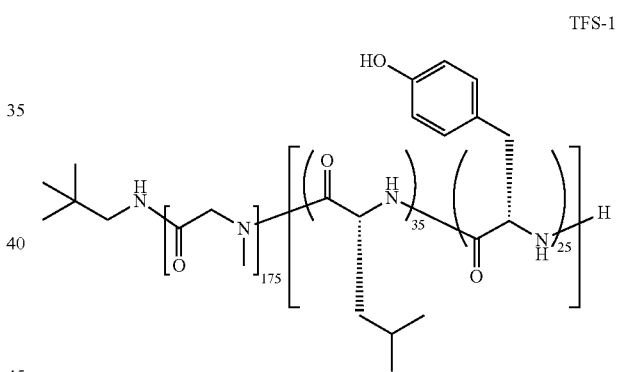

TFS-1

Another embodiment of the disclosure provides a multiblock copolymer represented by the following structure:

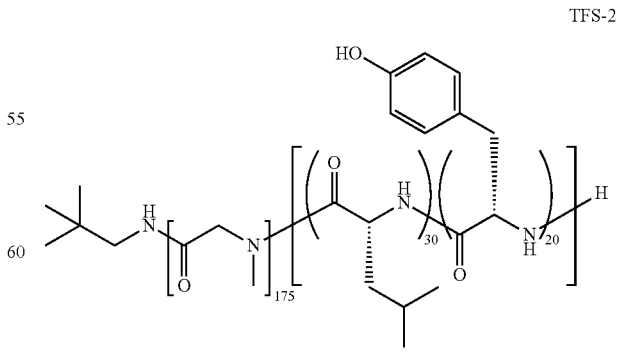

TFS-2

One embodiment of the disclosure provides a multiblock copolymer represented by the following structure:

One embodiment of the disclosure provides a multiblock copolymer represented by the following structure:

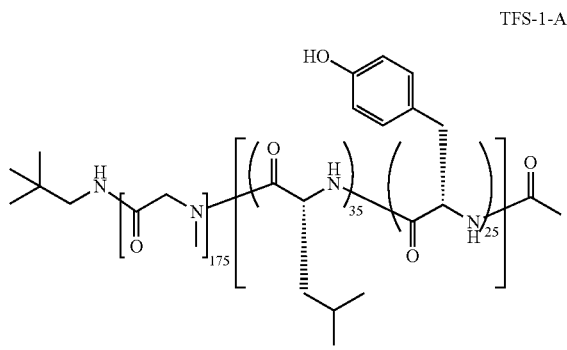

TFS-1-Ac

One embodiment of the disclosure provides a multiblock copolymer represented by the following structure:

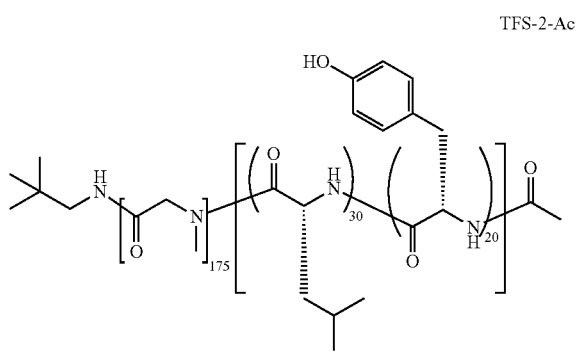

TFS-2-Ac

One embodiment of the disclosure provides a multiblock copolymer represented by the following structure:

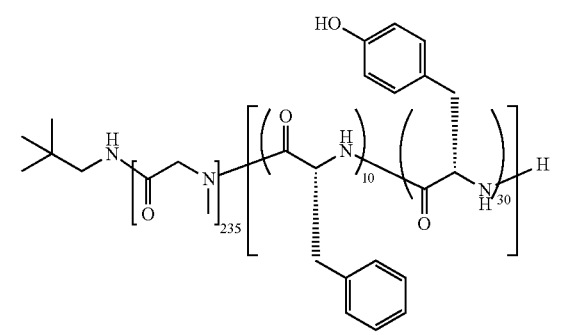

TFS-3

One embodiment of the disclosure provides a multiblock copolymer represented by the following structure:

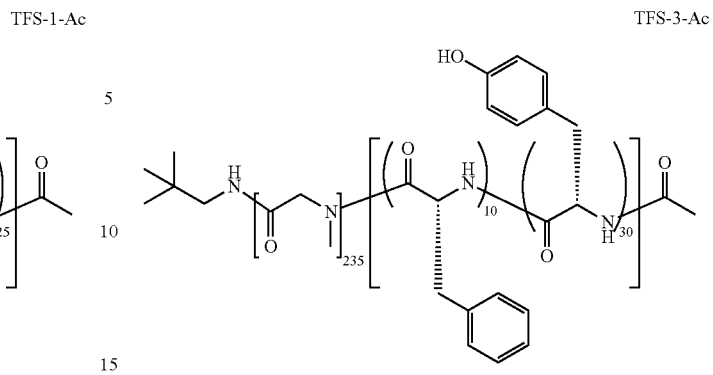

TFS-3-Ac

3.2 Synthesis of Multiblock Copolymers

In certain embodiments the disclosure provides methods for preparing multiblock copolymers comprising a poly(sarcosine) block and a D,L-mixed poly(amino acid) block. One embodiment of a general method for preparing said multiblock copolymers is depicted in Scheme 1 and comprises the following steps: 1) initiating polymerization of sarcosine NCA (Formula III) with a suitable amine-containing initiator (Formula II), 2) adding a mixture comprising one or more D-amino acid NCA (Formula IVy), and one or more L-amino acid NCA (Formula IVz) to the living polymerization.

Scheme 1

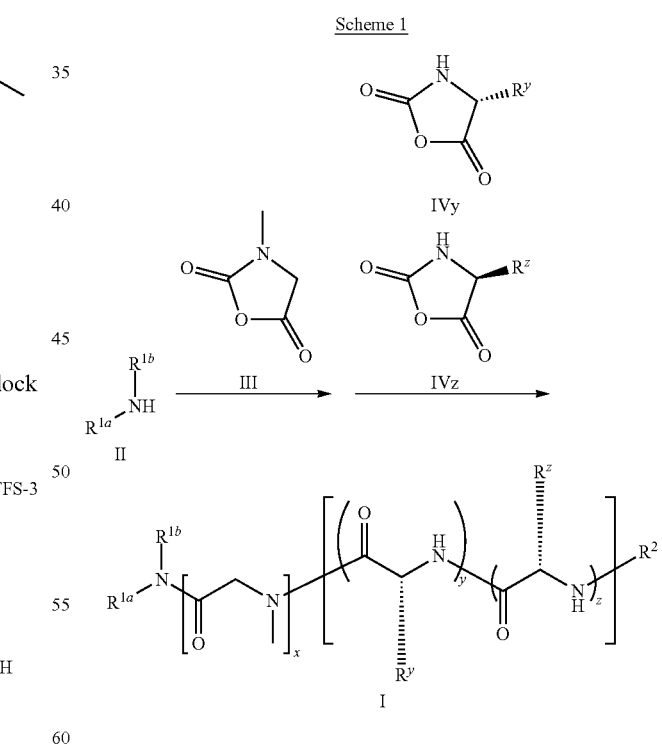

In some instances, it may be advantageous to add an NCA to the reaction as a solution rather than a solid. For example, during large-scale manufacturing when solutions are easier to handle than solids. In some embodiments of the present disclosure, an NCA, whether it be Formula III, Formula IVy, or Formula IVz, is added to the reaction as a solid. In another embodiment of the disclosure, an NCA, whether it be Formula III, Formula IVy, or Formula IVz, is added to the reaction as a solution. In certain embodiments, said solvent is the same solvent used to solubilize the initiator II. In a preferred embodiment, the solvent is N,N,-dimethylformamide. In another preferred embodiment, the solvent is N,N-dimethylacetamide.

As described herein, in certain embodiments, the D,L-mixed poly(amino acid) block of Formula I is prepared by the polymerization of NCAs derived from natural and unnatural amino acids. In some embodiments, the NCAs of Formula IVy and Formula IVz are selected such that the resulting poly(amino acid) block is hydrophobic overall. As discussed previously, the inclusion of an amino acid generally considered to be hydrophilic does not necessarily prevent the block from being hydrophobic overall. Accordingly, in certain embodiments the NCA of Formula IVy is derived from a hydrophilic D-amino acid, and the NCA of Formula IVz is derived from a hydrophobic L-amino acid. In other embodiments the NCA of Formula IVy is derived from a hydrophobic D-amino acid, and the NCA of Formula IVz is derived from a hydrophilic L-amino acid. In other embodiments the NCA of Formula IVy is derived from a hydrophobic D-amino acid, and the NCA of Formula IVz is derived from a hydrophobic L-amino acid.

In certain embodiments, the process depicted in Scheme 1 is performed in a single solvent. The solvent will be capable of solubilizing the starting materials, living polymerization chain, and the final copolymer such that all the material remains in solution during entire process. Amide containing solvents are suitable for this process. In a preferred embodiment the solvent is N,N-dimethylformamide (DMF). In another preferred embodiment, the solvent is N,N-dimethylacetamide (DMAc).

In certain embodiments, the initiator of Formula II is a primary amine, wherein $R^{1a}$ is a hydrogen and $R^{1b}$ is an optionally substituted aliphatic group. In certain embodiments, the initiator of Formula II is a secondary amine, wherein $R^{1a}$ is an optionally substituted aliphatic group and $R^{1b}$ is an optionally substituted aliphatic group. One skilled in the art will recognize that many primary and many secondary amines would be suitable for the initiation of a polymerization reaction with an NCA. Initiators envisioned by the present disclosure include, but are not limited to, optionally substituted benzylamines, optionally substituted hydrocarbon amines, optionally substituted silylamines, poly(amino acid) polymers, poly(ethylene glycol) polymers, poly(N-isopropylacrylamide) polymers, poly(acrylamide) polymers, poly(2-oxazoline) polymers, poly(ethylenimine), poly(acrylic acid) polymers, poly(methacrylate) polymers, poly(vinyl alcohol) polymers, poly(vinylpyrrolidone) polymers, and their corresponding amine salts. In a preferred embodiment, the initiator of Formula II is selected from benzylamine, p-methylbenzyl amine, p-methoxybenzylamine, or n-hexylamine. In a preferred embodiment the initiator of Formula II is neopentylamine represented by the following structure:

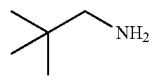

In some embodiments, the disclosure relates to a method to prepare a compound of Formula I using reagents, solvents, resins, and other components used in a chemical reaction or isolation as received. In some embodiments, a compound of Formula I is prepared without measures taken to exclude air and/or moisture (e.g. Schlenk techniques). Those skilled in the art will appreciate the advantage of NCA polymerization reactions under these conditions as it will reduce costs and increase the robustness of such processes.

The present disclosure also relates to the isolation of a multiblock copolymer of Formula I from a reaction mixture using a single anti-solvent. In some embodiments, the ratio of reaction mixture to anti-solvent is such to minimize the total amount used. Those skilled in the art will recognize that advantage of using a minimal amount of anti-solvent as it may reduce the cost and complexity and may increase the scale of preparation. Such reaction mixture to anti-solvent ratios contemplated by the present disclosure include, but are not limited to, 1:0.25, 1:0.5, 1:1, 1:1.5, 1:2, 1:3, 1:4, 1:5, 1:10.

The present disclosure relates to the use of a single reaction solvent and a single anti-solvent. Those skilled in the art will recognize that advantage of using only two solvents total for the preparation of a compound of Formula I, as this will minimize the costs, especially on commercial scale under Good Manufacturing Practice (GMP) guidance, as a minimal number of solvents will need to be sourced, and quantified during release testing. In certain embodiments the anti-solvent is selected from a list including, but not limited to, a ketone-containing solvent, a hydroxyl-containing solvent, an ester-containing solvent, an ether-containing solvent, a hydrocarbon solvent, an aromatic solvent, an aqueous solvent.

Anti-solvents envisioned in the disclosure include, but are not limited to, methyl ethyl ketone, acetone, butanone, ethanol, methanol, isopropanol, butanol, tert-butanol, methyl acetate, butyl acetate, diethyl ether, dioxane, tetrahydrofuran, hexane, heptane, toluene, benzene, water, aqueous buffer solutions.

In a preferred embodiment the anti-solvent is ethyl acetate. In another preferred embodiment, the anti-solvent is methyl tert-butyl ether.

As described above, $R^2$ for compounds of Formula I is an optionally substituted aliphatic group. Those skilled in the art will recognize that when $R^2$ is H (Formula IV), treatment with a terminating agent would be a method to alter the substitution at $R^2$. Such terminating agents, represented by $R^2$-LG in Scheme 2, include any $R^2$-containing group capable of reacting with terminal amine of a compound of Formula IV.

Scheme 2

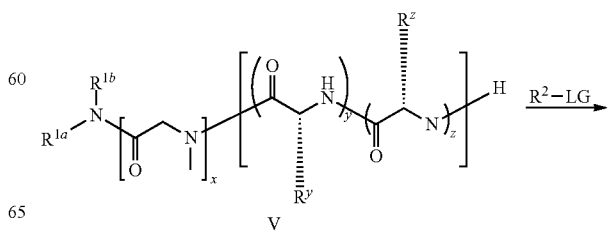

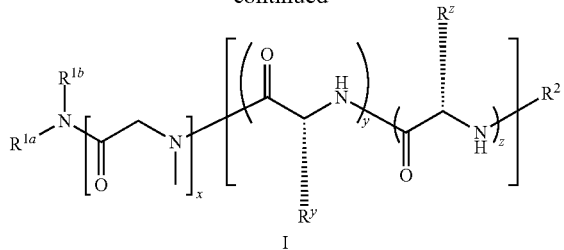

I

Those skilled in the art will recognize that many terminating agents of the structure $R^2$-LG are capable of reacting with the terminal amine of a compound represented by Formula V and its corresponding anion. Terminating agents of the structure $R^2$-LG envisioned by the disclosure include anhydrides, sulfonyl halides, and other acylating agents, and groups that contain a leaving group (LG) that is susceptible to nucleophilic displacement. In a preferred embodiment, the terminating agent is acetic anhydride represented by the following structure:

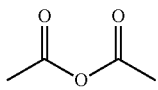

Those skilled in the art will recognize that treatment of a compound of Formula V with a terminating agent represented by $R^2$-LG, may be performed at the conclusion of an NCA polymerization which yields a compound of Formula V such that the method to prepare a compound of Formula I is performed as a "one-pot" synthesis. Alternatively, treatment with $R^2$-LG may be performed after isolation of a compound of Formula V from a reaction mixture in a "multi-step" process. In certain embodiments, a compound of Formula I is prepared in a one-pot process. In other embodiments, a compound of Formula I is prepared in a multi-step process.

3.3 Micelles

In certain embodiments, the present disclosure relates to polymeric micelles. It will be appreciated that multiblock poly(amino acid) copolymers comprising a hydrophilic block and a hydrophilic block will spontaneously self-assemble into micelles in aqueous solutions. One of ordinary skill in the art will recognize that a poly(sarcosine) block is hydrophilic. Without wishing to be bound by any particular theory, it is believed that a multiblock copolymer comprising poly(sarcosine) and a poly(amino acid) block that is hydrophobic overall will form a micelle with the poly(sarcosine) block forming a hydrophilic corona and the hydrophobic poly(amino acid) block forming the core of the micelle.

The poly(amino acid) block of the disclosure is comprised of a mixture of D- and L-amino acids. Without wishing to be bound by any particular theory, it is believed that the incorporation an atactic poly(amino acid) block disrupts the formation of secondary and tertiary structures normally adopted by isotactic poly(amino acids) such as proteins. This results in the formation of micelles constructed from atactic poly(amino acid)-containing copolymers having different physical properties than those of micelles constructed from equivalent isotactic poly(amino acid)-containing copolymers. Said physical properties include, but are not limited to, critical micelle concentration, solubility, and drug loading efficiency.

In certain embodiments, the disclosure relates to multi-block poly(amino acid) copolymers of Formula I which can self-assemble into multi-molecular micelles in aqueous solutions when their concentration is above the critical micelle concentration. Such micelles are useful for the encapsulating of hydrophobic molecules, including but not limited to, drugs, therapeutic agents, diagnostic agents, and probes.

3.4 Drug Loading

In certain embodiments, the disclosure relates to polymeric micelles which encapsulate a hydrophobic molecule, thus increasing the solubility of the molecule in aqueous solutions. Without wishing to be bound by any particular theory, it is believed that when a hydrophobic molecule is present with a multiblock copolymer of Formula I in an aqueous solution, the molecule will sequester in the hydrophobic portion of the multiblock copolymer and will have the effect of increasing the solubility of the hydrophobic molecule. When the multiblock copolymer forms a micelle, the hydrophobic molecule will be sequestered in the hydrophobic core of the micelle and will thus be rendered water-soluble by the hydrophilic corona of the micelle. In certain embodiments the hydrophobic molecule is a drug.

In some embodiments, the disclosure provides a composition comprising a hydrophobic molecule and a multiblock copolymer of Formula I. In some embodiments the hydrophobic molecule is a drug. In certain embodiments, the present disclosure provides drug loaded micelles in which the drug is selected from a list including, but not limited to, paclitaxel, docetaxel, cabazitaxel, and SN-38, and pharmaceutically acceptable salts thereof.

In some embodiments, the disclosure provides a composition comprising multiblock copolymer TFS-1 and a hydrophobic molecule. In a preferred embodiment the hydrophobic molecule is a drug selected from a list consisting of paclitaxel, docetaxel, cabazitaxel, and SN-38, and pharmaceutically acceptable salts thereof.

In some embodiments, the disclosure provides a composition comprising multiblock copolymer TFS-2 and a hydrophobic molecule. In a preferred embodiment the hydrophobic molecule is a drug selected from a list consisting of paclitaxel, docetaxel, cabazitaxel, and SN-38, and pharmaceutically acceptable salts thereof.

In some embodiments, the disclosure provides a composition comprising multiblock copolymer TFS-3 and a hydrophobic molecule. In a preferred embodiment the hydrophobic molecule is a drug selected from a list consisting of paclitaxel, docetaxel, cabazitaxel, and SN-38, and pharmaceutically acceptable salts thereof.

The weight loading of a particular hydrophobic molecule is dependent on the particular composition of a multiblock copolymer of Formula I. Those skilled in the art will recognize that a range of weight loadings for a hydrophobic molecule are possible with the present disclosure. It will also be recognized that the weight loading can be adjusted to meet the needs of a particular formulation, such as, solubility of the resulting formulation, stability, and reduction the cost of goods. In some embodiments, the hydrophobic molecule is a drug and the weight loading of said drug is between about 1% to about 25% of the composition.

In some embodiments, the disclosure provides compositions comprising a multiblock copolymer of Formula I and a drug,
wherein, the drug is about 1% to about 5% of the composition.

In some embodiments, the disclosure provides compositions comprising a multiblock copolymer of Formula I and a drug,
wherein, the drug is about 5% to about 10% of the composition.

In some embodiments, the disclosure provides compositions comprising a multiblock copolymer of Formula I and a drug,
wherein, the drug is about 10% to about 15% of the composition.

In some embodiments, the disclosure provides compositions comprising a multiblock copolymer of Formula I and a drug,
wherein, the drug is about 15% to about 20% of the composition.

In some embodiments, the disclosure provides compositions comprising a multiblock copolymer of Formula I and a drug,
wherein, the drug is about 20% to about 25% of the composition.

3.5 Drug Products

The disclosure provides compositions that are useful for encapsulating hydrophobic drugs, such compositions may be provided as drug products useful for the treatment of a patient in need thereof. In some embodiments, the disclosure provides drug products comprising a multiblock copolymer of Formula I, and a drug. Such compositions may further comprise an excipient, as defined herein.

Certain embodiments of the disclosure may be provided as pharmaceutically acceptable compositions. Such compositions include, but are not limited to, pills, tablets, capsules, aqueous suspensions or solutions, suppositories, creams, aerosols, syrups, film, skin patch, dermal patch, vaginal ring, eye drop. In a preferred embodiment the pharmaceutically acceptable composition is a lyophilized powder.

Compositions of the disclosure may provide a therapeutically effective amount of a drug suitable for the treatment of a subject in need thereof. In a preferred embodiment the subject is a human.

The disclosure also provides compositions that may be administered to a patient in need thereof. Routes of administration include, but are not limited to, parenterally, orally, sublingually, buccally, rectally, vaginally, by the ocular route, by the otic route, nasally, inhalation, nebulization, cutaneously, subcutaneously, topically, systemically, or transdermally. In some embodiments, the compositions of the disclosure may be formulated as part of an implant or device, or formulated for slow or extended release. In a preferred embodiment, the route of administration is intravenous. In another preferred embodiment the route of administration is via a central venous catheter. In another preferred embodiment the route of administration is via a peripheral venous catheter.

In certain embodiments of the disclosure, the compositions are formulated for oral administration, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and the like.

In solid dosage forms for oral administration (capsules, tablets, pills, dragees, powders, granules, and the like), the compositions of the disclosure may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

In some embodiments, the drug products of this disclosure are formulated as liquid dosage forms for oral administration. Liquid dosage forms for oral administration include pharmaceutically acceptable emulsions, microemulsions, solutions, suspensions, syrups and elixers. The liquid dosage forms may contain inert diluents commonly used in the art such as water or other solvents, solubilizing agents and emulsifiers, such as ethanol, isopropyl alcohol, ethyl carbonate, ethyl acetate, benzyl alcohol, benzyl benzoate, propylene glycol, 1,3-butyline glycol, oils (e.g., cottonseed, groundnut, corn, germ, olive, castor and sesame oils), glycerol, tetrahydrofuryl alcohol, polyethylene glycols and fatty acid esters or sorbitan and mixtures thereof. The oral compositions can also include adjuvants such as wetting agents, emulsifying and suspending agents, sweetening, flavoring, coloring, perfuming and preservative agents.

In certain embodiments, the compositions of the disclosure are formulated for parenteral administration. As an example, the compositions of the disclosure can be formulated for parenteral administration by further including one or more pharmaceutically acceptable sterile isotonic aqueous or non-aqueous solutions, dispersions, suspensions or emulsions, or sterile powders which may be reconstituted into sterile injectable solutions or dispersions just prior to use. The compositions for parenteral administration may contain antioxidants, buffers, bacteriostats, and/or solutes which render the formulation isotonic with the blood of the intended recipient or suspending or thickening agents. Examples of suitable aqueous and non-aqueous vehicles which may be employed in the pharmaceutical compositions of the disclosure include water, Ringer's solution, an isotonic salt solution, ethanol, polyols (such as 1,3-butanediol, glycerol, propylene glycol, polyethylene glycol, and the like), and suitable mixtures thereof, vegetable oils, such as olive oil, and injectable organic esters, such as ethyl oleate. In a preferred embodiment, the compositions of the disclosure are intended for parenteral administration, and further comprise a vehicle selected from water, 1,3-butanediol, Ringer's solution or an isotonic sodium chloride solution.

The compositions of the disclosure may be administered for slow, controlled or extended release. The term "extended release" is widely recognized in the art of pharmaceutical sciences and is used herein to refer to a controlled release of an active compound or agent from a dosage form to an environment over (throughout or during) an extended period of time, e.g. greater than or equal to one hour. An extended release dosage form will release drug at substantially constant rate over an extended period of time or a substantially constant amount of drug will be released incrementally over an extended period of time. The term "extended release" used herein includes the terms "controlled release," "prolonged release," "sustained release," "delayed release," or "slow release" as these terms are used in the pharmaceutical sciences. In some embodiments, the extended release dosage is administered in the form of a patch or a pump.

3.6 Process of Enhancing the Solubility of Hydrophobic Molecules

In certain embodiments, the present disclosure provides methods for increasing the solubility of hydrophobic molecules in aqueous solution. As described above the multi-block copolymers of the disclosure can spontaneously self-assemble into micellular structures in aqueous solutions with the hydrophilic poly(sarcosine) block forming the corona and the hydrophobic poly(amino acid) block forming the core of the micelle. If a hydrophobic molecule is present during this assembly, it can sequester (i.e., encapsulate) in the hydrophobic portion of the micelle. This will have the effect of increasing the solubility of the hydrophobic molecule in aqueous solutions.

In one aspect, the disclosure is directed to a method for increasing the solubility of a hydrophobic molecule in an aqueous solution comprising encapsulating the hydrophobic molecule in a multiblock copolymer according to this disclosure. One embodiment of the disclosure provides a method for preparing a composition comprising a hydrophobic molecule and a cryoprotective agent having enhanced solubility properties in aqueous solution. The general method for providing said composition comprises the steps of preparing a solution of a cryoprotectant and a multiblock copolymer according to the disclosure in water. Preparing a solution of a hydrophobic molecule in an organic solvent, thereby resulting in an organic solution. Adding said organic solution to said solution of a cryoprotectant and multiblock copolymer while shear mixing with a homogenizer to produce a homogenous emulsion. Processing said homogenous emulsion through a microfluidizer. Processing the microfluidizer extruded solution via tangential flow filtration against an aqueous solution of cryoprotectant. Sterile filtering the resulting solution (e.g. aseptic filtration), filing of vials under sterile conditions, and lyophilization under sterile conditions. Suitable cryoprotective agents include, but are not limited to: sugars, monosaccharides, disaccharides, polyalcohols, amino acids, glycine, polyvinyl pyrrolidine, polyethylene glycol, mannitol, sorbitol, sucrose, glucose, raffinose, sucralose, lactose, trehalose, dextran, and dextrose. In a preferred embodiment the cryoprotectant is trehalose.

3.8 Methods of Manufacture

In certain aspects, the disclosure is directed to methods for preparing drug products comprising a hydrophobic molecule and a copolymer of Formula I.

In some embodiments, the disclosure is directed to a method for preparing a sterile, lyophilized drug product comprising a hydrophobic molecule and a copolymer of Formula I. This drug product would be suitable for administration to a patient.

In some embodiments, the disclosure is directed to a method for preparing a sterile, lyophilized drug product comprising hydrophobic molecule, a copolymer of Formula I, and a cryoprotective agent. The general method for providing said drug product comprises the steps of preparing a solution of a cryoprotectant and a copolymer of Formula I in a mixture of aqueous tert-butanol. Preparing a solution of hydrophobic molecule in tert-butanol. Adding said hydrophobic molecule solution to said solution of a cryoprotectant and a copolymer of Formula I, sterile filtering the resulting solution (e.g. aseptic filtration), filing of vials under sterile conditions, and lyophilization under sterile conditions. Suitable cryoprotective agents include, but are not limited to: sugars, monosaccharides, disaccharides, polyalcohols, amino acids, mannitol, glycine, polyvinyl pyrrolidine, polyethylene glycol, sorbitol, sucrose, glucose, raffinose, sucralose, lactose, trehalose, dextran, and dextrose. In a preferred embodiment the cryoprotectant is trehalose or glycine.

In some embodiments, the disclosure is directed to a method of preparing a unit dosage form comprising:
a) dissolving a hydrophobic molecule, or a pharmaceutically acceptable salt thereof, a copolymer of Formula I and, optionally, a cryoprotectant, in aqueous tert-butanol, thereby forming a mixed solution; and
b) optionally lyophilizing the mixed solution.

In some embodiments, the disclosure is directed to a method of preparing a unit dosage form comprising:
a) dissolving hydrophobic molecule, or a pharmaceutically acceptable salt thereof, in tert-butanol, thereby forming a hydrophobic molecule solution;
b) dissolving a copolymer of Formula I and, optionally, a cryoprotectant, in an aqueous tert-butanol solution, thereby forming a copolymer solution;
c) mixing the hydrophobic molecule solution and the copolymer solution thereby forming a mixed solution; and
d) optionally lyophilizing the mixed solution.

In some embodiments, the disclosure is directed to a method of preparing a unit dosage form comprising:
a) dissolving hydrophobic molecule, or a pharmaceutically acceptable salt thereof, in tert-butanol, thereby forming a hydrophobic molecule solution;
b) dissolving a copolymer of Formula I and, optionally, a cryoprotectant, in an aqueous tert-butanol solution, thereby forming a copolymer solution;
c) mixing the hydrophobic molecule solution and the copolymer solution thereby forming a mixed solution;
d) filtering the mixed solution, thereby forming a filtered solution;
e) optionally lyophilizing the filtered solution.

In one aspect, the disclosure is directed to a method for preparing a sterile, lyophilized drug product comprising hydrophobic molecule and a copolymer of Formula I. This drug product would be suitable for administration to a patient. One embodiment of the disclosure provides a method for preparing a sterile, lyophilized drug product comprising a hydrophobic molecule, copolymer of Formula I, and a cryoprotective agent. The general method for providing said drug product comprises the steps of preparing a solution of a cryoprotectant and a copolymer of Formula I in water. Preparing a solution of a hydrophobic molecule in an organic solvent. Adding said hydrophobic molecule solution to said solution of a cryoprotectant and a copolymer of Formula I while shear mixing with a homogenizer to produce a homogenous emulsion. Processing said homogenous emulsion through a high shear mixer (e.g. microfluidizer). Processing the high shear mixer extruded solution via tangential flow filtration against an aqueous solution of cryoprotectant. Sterile filtering the resulting solution (e.g. aseptic filtration), filing of vials under sterile conditions, and lyophilization under sterile conditions. Suitable cryoprotective agents include, but are not limited to: sugars, monosaccharides, disaccharides, polyalcohols, amino acids, glycine, polyvinyl pyrrolidine, polyethylene glycol, mannitol, sorbitol, sucrose, glucose, raffinose, sucralose, lactose, trehalose, dextran, and dextrose. In a preferred embodiment the cryoprotectant is trehalose.

In some embodiments, the disclosure is directed to a method of preparing a unit dosage form comprising:
  a) dissolving a hydrophobic molecule, or a pharmaceutically acceptable salt thereof, a copolymer of Formula I and, optionally, a cryoprotectant, in an aqueous solution, thereby forming a mixed solution;
  b) processing the mixed solution through a high shear mixer, thereby forming a high shear mixed solution; and
  c) optionally lyophilizing the high shear mixed solution.

In some embodiments, the disclosure is directed to a method of preparing a unit dosage form comprising:
  a) dissolving a hydrophobic molecule, or a pharmaceutically acceptable salt thereof, in an organic solvent, thereby forming a hydrophobic molecule solution;
  b) dissolving a copolymer of Formula I and, optionally, a cryoprotectant, in an aqueous solution, thereby forming a copolymer solution;
  c) mixing the hydrophobic molecule solution and the copolymer solution, thereby forming a mixed solution;
  d) processing the mixed solution through a high shear mixer, thereby forming a high shear mixer solution;
  e) filtering the high shear mixer solution, thereby forming a filtered solution; and f) optionally lyophilizing the filtered solution.

In some embodiments, the disclosure is directed to a method of preparing a unit dosage form comprising:
  a) dissolving a hydrophobic molecule, or a pharmaceutically acceptable salt thereof, in an organic solvent, thereby forming a hydrophobic molecule solution;
  b) dissolving a copolymer of Formula I and, optionally, a cryoprotectant, in an aqueous solution, thereby forming a copolymer solution;
  c) mixing the hydrophobic molecule solution and the copolymer solution, thereby forming a mixed solution;
  d) processing the mixed solution through a high shear mixer, thereby forming a high shear mixer solution;
  e) processing the high shear mixer solution with a diafiltration system, thereby forming a diafiltered solution;
  f) filtering the diafiltered solution, thereby forming a filtered solution; and
  g) optionally lyophilizing the filtered solution.

3.7 Specific Examples

The present disclosure envisions multiblock copolymers of the following structures:

VI

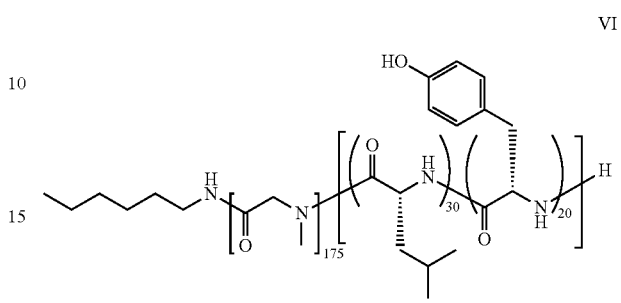

VII

VIII

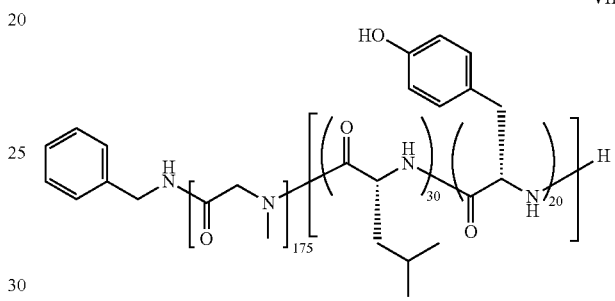

IX

X

XI
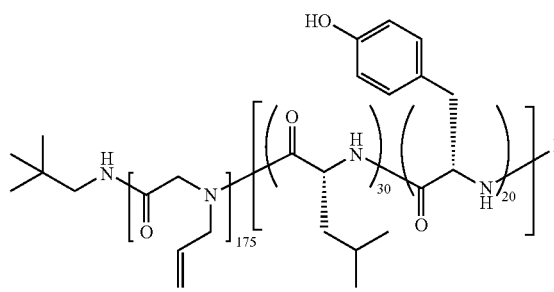
XII
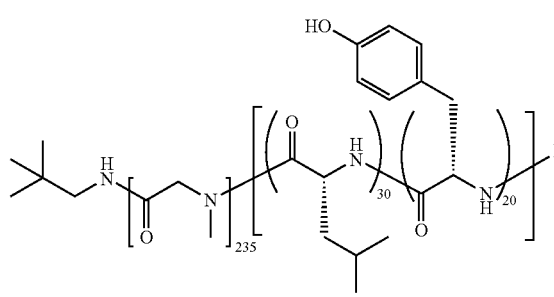
XIII
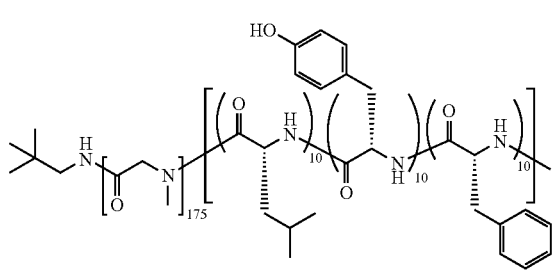
XIV
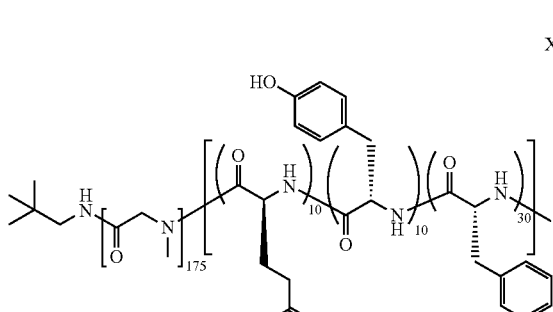
XV
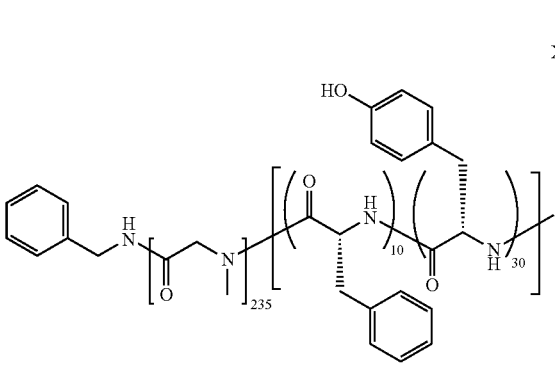
XVI
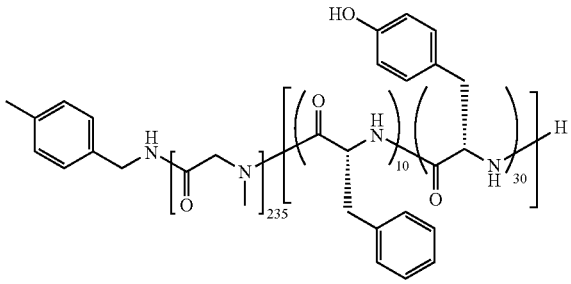
XVII
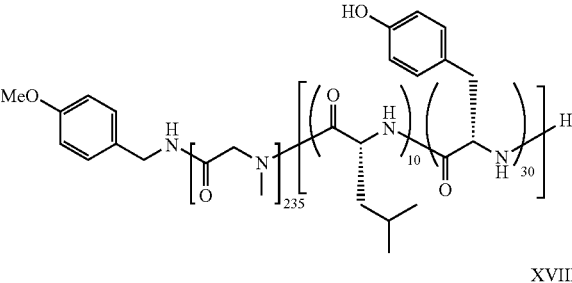
XVIII
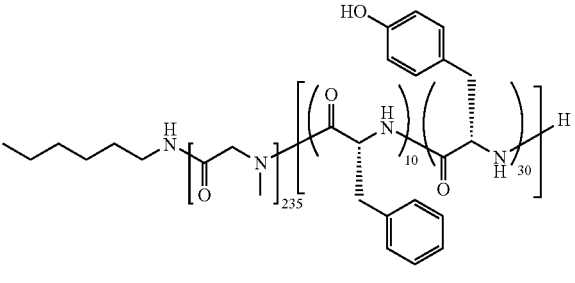
XIX
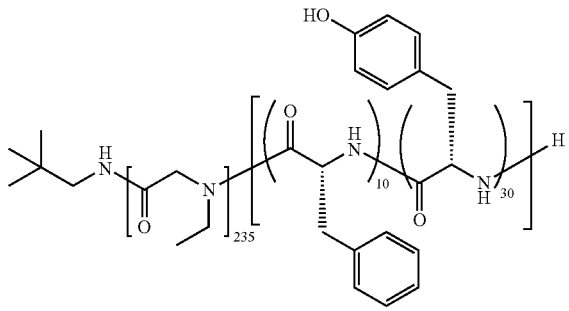
XX
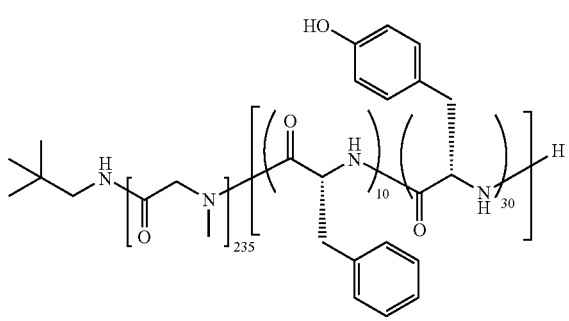

XXI
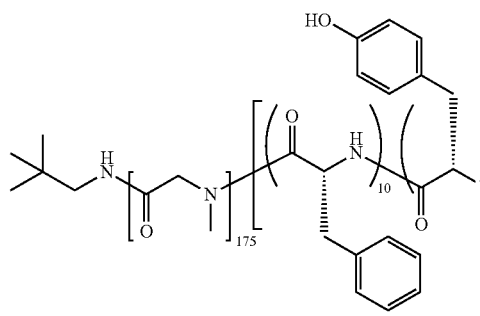

XXII
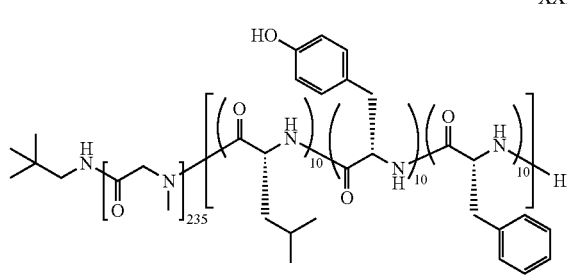

XXIII
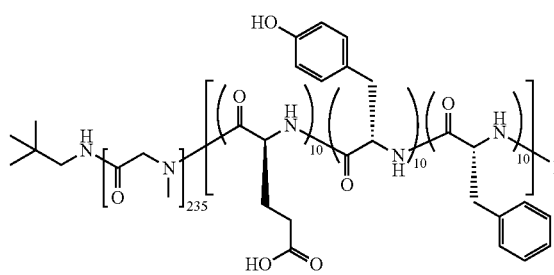

XXIV
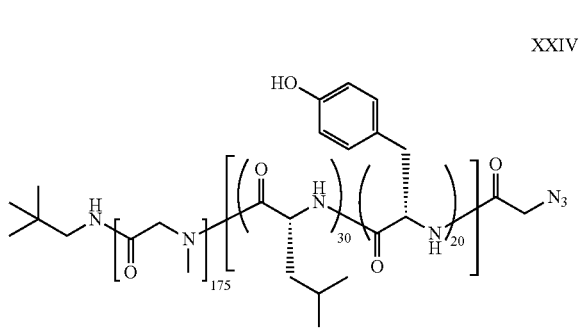

XXV
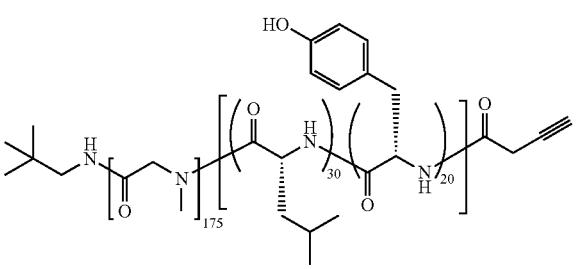

XXVI
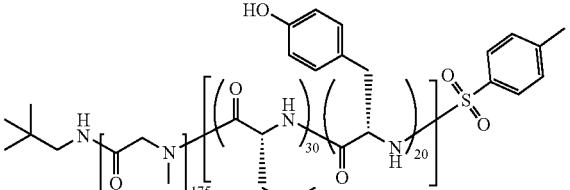

XXVII
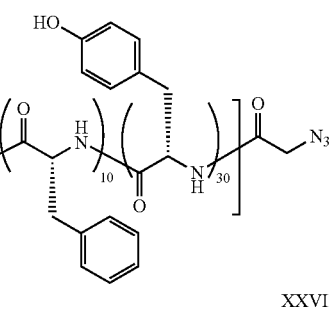

XXVIII
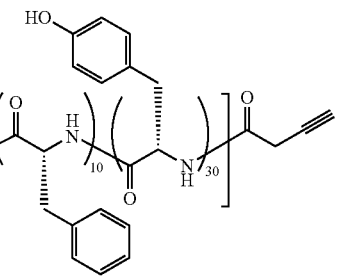

XXIX
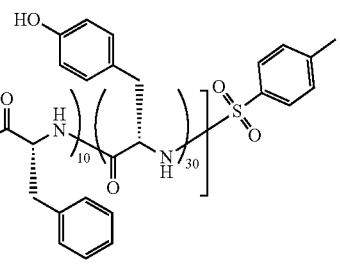

Exemplification

In order for the disclosure to be more fully understood, the following examples are set forth. It will be understood that these examples are for illustrative purposes only and are not to be construed as limiting this disclosure in any manner.

In the Examples, where an amino acid or NCA contains the "D" prefix, then the corresponding amino acid or NCA is the D-configuration. Where no such prefix is present, the corresponding amino acid or NCA is the L-configuration.

In the Examples, unless otherwise stated, all multiblock copolymers are understood to begin with a neopentylamino group $(CH_3)_3CH_2$—NH—, despite not being explicitly including in the short-hand description. For example, $Sar_x$-b-p-[D-Leu$_y$-co-L-Tyr$_z$] is the short-hand description of the following compound:

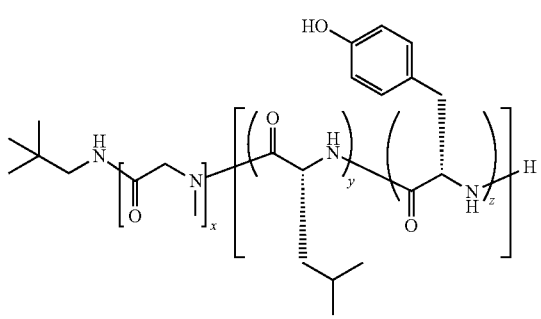

Analytical Methods

The following analytical methods were utilized to characterize the compounds of the present disclosure.

Infrared (IR) Spectroscopy—All samples were analyzed using a PerkinElmer Spectrum 100 FT-TR Spectrometer equipped with Universal ATR Sampling Accessory (Diamond/ZnSe). When using TR to monitor a reaction, an aliquot of approximately 100 μL was taken and measured directly. Solid samples were measured without further manipulation.

Nuclear Magnetic Resonance (NMR) Spectroscopy—All samples were analyzed in a 400 MHz spectrometer with the following parameters: 45° pulse, 2 second acquisition time, 5 second recycle delay, with 16-32 transients.

Gel Permeation Chromatography (GPC) Analysis—Samples were analyzed using a Shimadzu LC-20AD pump connected in series to: 2×PSS GRAM analytical 100 Å, 8×300 mm, 10 μm columns; 1×PSS GRAM analytical 1000 Å, 8×300 mm, 10 μm column; a Wyatt TREOS II Light Scattering Detector, and a Wyatt Optilab T-rEX refractive index detector. A mobile phase of DMF supplemented with LiBr (50 mM) at a flow rate of 1.0 mL was used to elute the analytes. The temperature of the columns was maintained at 45° C. Typically, run times of 45 minutes were employed. GPC number-average molecular weight (Mn) and peak molecular weight (Mp) were calibrated using polystyrene molecular weight standards.

Paclitaxel HPLC Method—Assay and identity of paclitaxel was determined by high pressure liquid chromatography with UV detection at 227 nm. The column utilized was a Phenomenex Gemini® 5 μm C18 (110 Å, 250×4.6 mm) at ambient temperature. The mobile phase consisted of a 60:40 (v/v) mixture of 10 mM sodium phosphate and acetonitrile. Paclitaxel drug product samples were prepared by dissolving the material in the mobile phase. Paclitaxel standards were prepared by dissolving the material in acetonitrile. Separation was achieved with a flow rate of 1.0 mL/min for a total run time of 12 minutes.

Cabazitaxel HPLC Method—Assay and identity of cabazitaxel was determined by high pressure liquid chromatography with UV detection at 227 nm. The column utilized was a Phenomenex Gemini® 5 μm C18 (110 Å, 250×4.6 mm) at ambient temperature. The mobile phase consisted of a 60:40 (v/v) mixture of 10 mM sodium phosphate and acetonitrile. Cabazitaxel drug product samples were prepared by dissolving the material in the mobile phase. Cabazitaxel standards were prepared by dissolving the material in acetonitrile. Separation was achieved with a flow rate of 1.0 mL/min for a total run time of 8 minutes.

Docetaxel HPLC Method—Assay and identity of docetaxel was determined by high pressure liquid chromatography with UV detection at 227 nm. The column utilized was a Phenomenex Gemini® 5 μm C18 (110 Å, 250×4.6 mm) at ambient temperature. The mobile phase consisted of a 60:40 (v/v) mixture of 10 mM sodium phosphate and acetonitrile. Docetaxel drug product samples were prepared by dissolving the material in the mobile phase. Docetaxel standards were prepared by dissolving the material in acetonitrile. Separation was achieved with a flow rate of 1.0 mL/min for a total run time of 8 minutes.

SN-38 HPLC Method—Assay and identity of SN-38 was determined by high pressure liquid chromatography with UV detection at 265 nm. The column utilized was a Phenomenex Gemini® 5 μm C18 (110 Å, 250×4.6 mm) at ambient temperature. The mobile phase consisted of a 70:30 (v/v) mixture of 10 mM sodium phosphate with 0.1% (v/v) triethylamine, pH 3.5 and acetonitrile. SN-38 drug product samples and standards were prepared by dissolving the material in a 7:3 (v/v) mixture of acetonitrile and DMSO. Separation was achieved with a flow rate of 1.5 mL/min for a total run time of 8 minutes.

Paclitaxel Weigh Loading Analysis—Weight loading was determined by comparing a standard curve of paclitaxel to a known concentration of drug product by HPLC analysis. Standards were prepared by dissolving paclitaxel in acetonitrile at concentrations of 10, 25, 50, 100, and 200 μg/mL. Paclitaxel drug product samples were prepared by dissolving the material in the mobile phase at a concentration of 1 mg/mL. The amount of paclitaxel in the drug product is then converted to weight percentage of the total based on the known quantity of drug product (i.e. 1 mg/mL).

SN-38 Weigh Loading Analysis—Weight loading was determined by comparing a standard curve of SN-38 to a known concentration of drug product by HPLC analysis. Standards were prepared by dissolving SN-38 in a 7:3 (v/v) mixture of acetonitrile and DMSO at concentrations of 50, 100, 200, 300, and 400 μg/mL. SN-38 drug product samples were prepared by dissolving the material in a 7:3 (v/v) mixture of acetonitrile and DMSO at a concentration between 1-4 mg/mL depending on the weight loading. The amount of SN-38 in the drug product is then converted to weight percentage of the total based on the known quantity of drug product.

Cabazitaxel Weigh Loading Analysis—Weight loading was determined by comparing a standard curve of cabazitaxel to a known concentration of drug product by HPLC analysis. Standards were prepared by dissolving cabazitaxel in acetonitrile at concentrations of 20, 40, 60, 80, and 100 μg/mL. Cabazitaxel drug product samples were prepared by dissolving the material in the mobile phase at a concentration of 1 mg/mL. The amount of cabazitaxel in the drug product is then converted to weight percentage of the total based on the known quantity of drug product (i.e. 1 mg/mL).

Docetaxel Weigh Loading Analysis—Weight loading was determined by comparing a standard curve of docetaxel to a known concentration of drug product by HPLC analysis. Standards were prepared by dissolving docetaxel in acetonitrile at concentrations of 10, 50, and 100 μg/mL. Docetaxel drug product samples were prepared by dissolving the material in the mobile phase at a concentration of 1 mg/mL. The amount of docetaxel in the drug product is then converted to weight percentage of the total based on the known quantity of drug product (i.e. 1 mg/mL).

Rat Paclitaxel Pharmacokinetic Experiments—Sprague-Dawley rats (3 male and 3 female per test article) sourced from Hilltop Lab Animals were used by WuXi AppTec for the study. The TYN-21 paclitaxel formulation (100 mg of 13 weight % paclitaxel) was reconstituted in saline (5.2 mL) to provide a solution with a paclitaxel concentration of 2.50 mg/mL. Abraxane was reconstituted with 20 mL of saline according the package insert to provide a solution of 5 mg/mL paclitaxel which was diluted 1:1 (v/v) with saline to provide a solution with a paclitaxel concentration of 2.5 mg/mL. Both the TYN-21 and Abraxane solutions were administered at 2.0 mL/kg by fast bolus IV infusion over 1-2 minutes via the tail vein to deliver a paclitaxel dose of 5.0 mg/kg. Blood samples (~300 µL) were collected from jugular veins into BD Microtainer tubes containing $K_2$EDTA at the end of infusion (EOI), and after 1 hour, 2 hours, 4 hours, and 8 hours. The blood samples were centrifuged at 4° C., 3000 g for 5 minutes within 30 minutes of collection. Plasma was collected into polypropylene tubes or 96-well plates, quickly frozen on dry ice and stored at −70±10° C. until LC-MS/MS analysis. Quantification was determined by comparing a standard curve (6 non-zero concentrations) of paclitaxel in plasma against the samples from each time point. Abraxane demonstrated a paclitaxel AUC of 4,648±1, 306 ng*h/mL. The $C_{max}$ of paclitaxel from Abraxane was 20,067±8,069 ng/mL. The half-life of paclitaxel from Abraxane was 3.1±0.6 h. The clearance of paclitaxel from Abraxane was 18.4±5.3 mL/min/kg. TYN-21 demonstrated a paclitaxel AUC of 5,873±2,103 ng*h/mL. The $C_{max}$ of paclitaxel from TYN-21 was 18,367±7,410 ng/mL. The half-life of paclitaxel from TYN-21 was 3.2±0.4 h. The clearance of paclitaxel from TYN-21 was 15.3±4.6 mL/min/kg. The pharmacokinetic data is shown in the drawing.

Example 1—Preparation of $Sar_{175}$-b-p-[$D$-$Leu_{35}$-co-$L$-$Tyr_{25}$] (TFS-1)

The A jacketed round-bottom flask equipped to a circulating isopropanol/water bath was charged with N,N-dimethylformamide (100 mL). The bath temperature was set to 20° C. and stirred for ~15 mins to equilibrate before the addition of a solution of neopentylamine (3.31 mL of 300 mM in DMF, 86.6 mg, 1 equiv.) followed by the addition of sarcosine N-carboxyanhydride (20.0 g, 173.8 mmol, 175 equiv.). The sides of the funnel and reaction vessel were rinsed down with additional DMF (~5 mL). The reaction vessel was wrapped in aluminum foil to prevent light. As the reaction proceeds, the color changes from clear and colorless to a clear, bright orange solution. IR was used to monitor the reaction progression via disappearance of the carbonyl stretches at ~1850 and 1778 cm$^{-1}$. After 8 hours the reaction was >95% complete but was left overnight (additional 12 hrs). The bath temperature was set to 25° C. and then the reaction was charged with D-leucine N-carboxyanhydride (5.46 g, 34.77 mmol, 35 equiv.) and L-tyrosine N-carboxyanhydride (5.15 g, 24.84 mmol, 25 equiv.). The consumption of the two NCAs again monitored via the disappearance of the IR carbonyl stretches at ~1851 and 1785 cm$^{-1}$, and the was complete after ~24 hrs. The reaction mixture was transferred to a beaker using a small amount of DMF (~5-10 mL) to help. While stirring vigorously with an overhead stirrer, ethyl acetate (480 mL, ~4 volumes) was added slowly over 1-2 mins. The precipitation is quick and noticeable solids start to form after the addition of <1 volume of EtOAc. The precipitation was stirred for 5-10 mins to help mechanical break apart any large solids to help leach out DMF which can become trapped in the solids. The stirring was stopped, and the material was allowed to settle before collected via vacuum filtration in a medium porosity fritted glass funnel. The semi-dry material was slurried briefly on the frit with an additional 2 volumes (240 mL) of EtOAc. The product was dried in vacuum oven at 90-100° C. for 2 days to yield 19.8 g (97%) of the title compound as a fine off-white dense powder. $^1$H NMR (DMSO-$d_6$) δ 9.2-9.0 (30H), 8.6-7.8 (48H), 7.2-6.5 (125H), 4.7-3.7 (845H), 3.0-2.6 (1440H), 1.9-1.2 (104H), 1.0-0.5 (289H); GPC (DMF, 50 mM LiBr) Mn=17.6 kDa, Mp=18.7 kDa, PDI=1.08.

Example 2—Preparation of $Sar_{175}$-b-p-[$D$-$Leu_{30}$-co-$L$-$Tyr_{20}$] (TFS-2)

A jacketed round-bottom flask equipped to a circulating isopropanol/water bath was cooled to 20° C. prior to the addition of sarcosine N-carboxyanhydride (19.9 g, 172.9 mmol, 175 equiv.), followed by N,N-dimethylformamide (100 mL). The mixture was stirred for <30 seconds before the addition of neopentylamine (3.30 mL of 300 mM in DMF, 86.2 mg, 1 equiv.). The reaction vessel was wrapped in aluminum foil to prevent exposure to light. After 15-20 mins, the reactions started to change from the initial clear and colorless solution to a light orange color that continues to intensify as the reaction proceeds. IR was used to monitor the reaction progression via disappearance of the Sar NCA carbonyl stretches at ~1850 and 1778 cm$^1$, with the latter being the preferred wavenumber to monitor. The reaction was ~90% done after 6 hrs but was left to stir overnight. The next day, after a total of 19 hrs the reaction was complete. The circulating bath temperature was increased to 25° C. prior to the addition of D-leucine N-carboxyanhydride (4.66 g, 29.66 mmol, 30 equiv.) and L-tyrosine N-carboxyanhydride (4.10 g, 19.78 mmol, 20 equiv.). Additional DMF (~5 mL) was used to rinse down the sides of the funnel and reaction vessel. Significant $CO_2$ gas formation was observed shortly after the reaction was initiated. IR was used to monitor the reaction progression via disappearance of the D-Leu NCA and L-Tyr NCA carbonyl stretches at ~1851 and 1785 cm$^{-1}$, with the latter being the preferred wavenumber to monitor. As the reaction proceeds, the color changed from a clear bright orange to a clear yellow-orange solution that was apparent after only a few hours. The reaction was >85% complete after 10 hrs, and >99.9% complete after 24 hrs. The reaction mixture (total of ~125 mL) was transferred to a beaker and fitted with an overhead stirrer. While vigorously stirring, ethyl acetate (250 mL, 2 volumes) was added to precipitate the product. The solids were collected via filtration into a medium fritted glass funnel. The solids were transferred back to the original precipitation beaker along with additional EtOAc (250 mL) and slurried with vigorous stirring for 20 mins. The solids were collected in a new fritted glass funnel and then the same 20 mins slurrying procedure with was repeated with EtOAc (250 mL) once more. The product was dried on the frit in a vacuum oven at 90-100° C. to yield 15.95 g (84.1%) of the title compound as a fine off-white dense powder. $^1$H NMR (DMSO-$d_6$) δ 9.2-8.9 (21H), 8.6-7.6 (39H), 7.2-6.4 (100H), 4.7-3.7 (694H), 3.1-2.6 (1039H), 1.9 (3H), 1.7-1.2 (33H), 1.0-0.6 (186H); GPC (DMF, 50 mM LiBr) Mn=16.9 kDa, Mp=18.0 kDa, PDI=1.08.

Example 3—Preparation of $Sar_{175}$-b-p-[$D$-$Leu_{30}$-co-$L$-$Tyr_{20}$]-Ac (TFS-2-Ac)

A round-bottom flask was charged with TFS-2 (500 mg, 0.0261 mmol, 1 equiv.) and N,N-dimethylformamide (5.0 mL) and the mixture was stirred and heated with a heat gun to dissolve the material. Once the reaction mixture cooled to ambient temperature, triethylamine (36 µL, 0.261 mmol, 10 equiv.) and acetic anhydride (25 µL, 0.261 mmol, 10 equiv.) were added. The reaction was stirred for 24 h before being transferred to a beaker using a minimum amount of N,N-dimethylformamide (~1.5 mL) to assist in the transfer. With vigorous stirring, a large excess of ethyl acetate (40 mL) was added over 1 min. The precipitation was stirred for 5 min before the solids were collected in a fritted glass funnel. The product was washed on the funnel with additional ethyl acetate (2×40 mL) and then dried at 95° C. for 48 h to yield the title compound as a granular white powder (320 mg, 64.0%). $^1$H NMR (DMSO-d$_6$) δ 9.2-9.0 (16H), 8.8-7.5 (54H), 7.5-6.4 (100H), 4.7-3.7 (843H), 3.2-2.6 (1272H), 2.2 (24H), 1.8-1.0 (96H), 1.0-0.4 (211H).

Example 4—Preparation of Sar$_{125}$-b-p-[D-Glu(OBn)$_{15}$-co-L-Glu(OBn)$_{15}$]

Following the general procedure of Example 1 with the following reagent equivalents and amounts: neopentylamine (30 mg, 1 equiv.), sarcosine NCA (4.95 g, 125 equiv.), D-Glu(OBn) NCA (1.36 g, 15 equiv.), and L-Glu(OBn) (1.36 g, 15 equiv.). This yielded the title compound as a light yellow solid (4.6 g, 86%). GPC (DMF, 50 mM LiBr) Mn=13.9 kDa, Mp=14.9 kDa, PDI=1.15.

Example 5—Preparation of Sar$_{125}$-b-p-[D-Glu(OBn)$_{20}$-co-L-Glu(OBn)$_{20}$]

Following the general procedure of Example 1 with the following reagent equivalents and amounts: neopentylamine (30 mg, 1 equiv.), sarcosine NCA (4.95 g, 125 equiv.), D-Glu(OBn) NCA (1.81 g, 20 equiv.), and L-Glu(OBn) (1.81 g, 20 equiv.). This yielded the title compound as a light yellow solid (4.9 g, 80%). GPC (DMF, 50 mM LiBr) Mn=14.6 kDa, Mp=15.6 kDa, PDI=1.11.

Example 6—Preparation of Sar$_{125}$-b-p-[D-Phe$_{15}$-co-L-Tyr$_{15}$]

Following the general procedure of Example 1 with the following reagent equivalents and amounts: neopentylamine (30 mg, 1 equiv.), sarcosine NCA (4.95 g, 125 equiv.), D-Phe NCA (0.987 g, 15 equiv.), and L-Tyr (1.07 g, 15 equiv.). This yielded the title compound as a light yellow solid (3.9 g, 83%). GPC (DMF, 50 mM LiBr) Mn=13.7 kDa, Mp=14.5 kDa, PDI=1.03.

Example 7—Preparation of Sar$_{125}$-b-p-[D-Leu$_{20}$-co-L-Tyr$_{15}$]

Following the general procedure of Example 1 with the following reagent equivalents and amounts: neopentylamine (30 mg, 1 equiv.), sarcosine NCA (4.95 g, 125 equiv.), D-Leu NCA (1.08 g, 20 equiv.), and L-Tyr (1.07 g, 15 equiv.). This yielded the title compound as a light yellow solid (3.7 g, 79%). GPC (DMF, 50 mM LiBr) Mn=15.1 kDa, Mp=16.1 kDa, PDI=1.09.

Example 8—Preparation of Sar$_{175}$-b-p-[D-Glu(OBn)$_{25}$-co-L-Glu(OBn)$_{25}$]

Following the general procedure of Example 1 with the following reagent equivalents and amounts: neopentylamine (43 mg, 1 equiv.), sarcosine NCA (10.0 g, 175 equiv.), D-Glu(OBn) NCA (3.27 g, 25 equiv.), and L-Glu(OBn) (3.27 g, 25 equiv.). This yielded the title compound as a light yellow solid (10 g, 86%). GPC (DMF, 50 mM LiBr) Mn=15.9 kDa, Mp=16.9 kDa, PDI=1.06.

Example 9—Preparation of Sar$_{175}$-b-p-[D-Phe$_{20}$-co-L-Tyr$_{20}$]

Following the general procedure of Example 1 with the following reagent equivalents and amounts: neopentylamine (43 mg, 1 equiv.), sarcosine NCA (10.0 g, 175 equiv.), D-Phe NCA (1.90 g, 20 equiv.), and L-Tyr (2.06 g, 20 equiv.). This yielded the title compound as a light yellow solid (7.8 g, 85%). GPC (DMF, 50 mM LiBr) Mn=14.9 kDa, Mp=15.9 kDa, PDI=1.04.

Example 10—Preparation of Sar$_{175}$-b-p-[Sar$_{10}$-co-L-Tyr$_{50}$]

Following the general procedure of Example 1 with the following reagent equivalents and amounts: neopentylamine (43 mg, 1 equiv.), sarcosine NCA (first block, 10.0 g, 175 equiv.), sarcosine NCA (0.57 g, 10 equiv.), and L-Tyr (5.14 g, 50 equiv.). This yielded the title compound as a light yellow solid (10.1 g, 96%). GPC (DMF, 50 mM LiBr) Mn=15.5 kDa, Mp=16.4 kDa, PDI=1.15.

Example 11—Preparation of Sar$_{175}$-b-p-[D-Phe$_{25}$-co-L-Glu(OBn)$_{25}$]

Following the general procedure of Example 1 with the following reagent equivalents and amounts: neopentylamine (21.7 mg, 1 equiv.), sarcosine NCA (4.98 g, 175 equiv.), D-Phe NCA (1.19 g, 25 equiv.), and L-Glu(OBn) (1.64 g, 25 equiv.). This yielded the title compound as a light yellow solid (3.8 g, 71%). GPC (DMF, 50 mM LiBr) Mn=16.3 kDa, Mp=17.4 kDa, PDI=1.09.

Example 12—Preparation of Sar$_{175}$-b-p-[D-Phe$_{30}$-co-L-Tyr$_{10}$]

Following the general procedure of Example 1 with the following reagent equivalents and amounts: neopentylamine (21.7 mg, 1 equiv.), sarcosine NCA (4.98 g, 175 equiv.), D-Phe NCA (1.43 g, 30 equiv.), and L-Tyr (0.515 g, 10 equiv.). This yielded the title compound as a light yellow solid (4.26 g, 92.4%). GPC (DMF, 50 mM LiBr) Mn=15.9 kDa, Mp=16.9 kDa, PDI=1.60.

Example 13—Preparation of Sar$_{175}$-b-p-[D-Phe$_{10}$-co-L-Tyr$_{30}$]

Following the general procedure of Example 1 with the following reagent equivalents and amounts: neopentylamine (21.7 mg, 1 equiv.), sarcosine NCA (4.98 g, 175 equiv.), D-Phe NCA (0.475 g, 10 equiv.), and L-Tyr (1.54 g, 30 equiv.). This yielded the title compound as a light yellow solid (4.66 g, 99.3%). GPC (DMF, 50 mM LiBr) Mn=16.1 kDa, Mp=17.1 kDa, PDI=1.07.

Example 14—Preparation of Sar$_{175}$-b-p-[D-Phe$_{25}$-co-L-Tyr$_{15}$]

Following the general procedure of Example 1 with the following reagent equivalents and amounts: neopentylamine (21.7 mg, 1 equiv.), sarcosine NCA (5.0 g, 175 equiv.), D-Phe NCA (1.19 g, 25 equiv.), and L-Tyr (0.772 g, 15 equiv.). This yielded the title compound as a light yellow solid (4.37 g, 94.3%). GPC (DMF, 50 mM LiBr) Mn=14.1 kDa, Mp=15.0 kDa, PDI=1.54.

Example 15—Preparation of Sar$_{175}$-b-p-[D-Phe$_{15}$-co-L-Tyr$_{25}$]

Following the general procedure of Example 1 with the following reagent equivalents and amounts: neopentylamine (21.7 mg, 1 equiv.), sarcosine NCA (5.0 g, 175 equiv.), D-Phe NCA (0.712 g, 15 equiv.), and L-Tyr (1.29 g, 25 equiv.). This yielded the title compound as a light yellow solid (4.57 g, 97.7%). GPC (DMF, 50 mM LiBr) Mn=14.4 kDa, Mp=15.3 kDa, PDI=1.07.

Example 16—Preparation of Sar$_{210}$-b-p-[D-Phe$_{15}$-co-L-Tyr$_{25}$]

Following the general procedure of Example 1 with the following reagent equivalents and amounts: neopentylamine (18 mg, 1 equiv.), sarcosine NCA (5.0 g, 210 equiv.), D-Phe NCA (0.593 g, 15 equiv.), and L-Tyr (1.07 g, 25 equiv.). This yielded the title compound as a light yellow solid (3.43 g, 78.0%). GPC (DMF, 50 mM LiBr) Mn=17.0 kDa, Mp=18.1 kDa, PDI=1.06.

Example 17—Preparation of Sar$_{210}$-b-p-[D-Phe$_{10}$-co-L-Tyr$_{30}$]

Following the general procedure of Example 1 with the following reagent equivalents and amounts: neopentylamine (18 mg, 1 equiv.), sarcosine NCA (5.0 g, 210 equiv.), D-Phe NCA (0.396 g, 10 equiv.), and L-Tyr (1.29 g, 30 equiv.). This yielded the title compound as a light yellow solid (3.62 g, 82.0%). GPC (DMF, 50 mM LiBr) Mn=17.0 kDa, Mp=18.1 kDa, PDI=1.08.

Example 18—Preparation of Sar$_{210}$-b-p-[D-Phe$_{5}$-co-L-Tyr$_{35}$]

Following the general procedure of Example 1 with the following reagent equivalents and amounts: neopentylamine (18 mg, 1 equiv.), sarcosine NCA (5.0 g, 210 equiv.), D-Phe NCA (0.198 g, 5 equiv.), and L-Tyr (1.50 g, 35 equiv.). This yielded the title compound as a light yellow solid (3.64 g, 82.2%). GPC (DMF, 50 mM LiBr) Mn=16.8 kDa, Mp=17.8 kDa, PDI=1.13.

Example 19—Preparation of Sar$_{235}$-b-p-[D-Phe$_{10}$-co-L-Tyr$_{30}$] (TFS-3)

A jacketed round-bottom flask equipped to a circulating isopropanol/water bath was cooled to 20° C. prior to the addition of sarcosine N-carboxyanhydride (15.0 g, 130.5 mmol, 235 equiv.), followed by N,N-dimethylformamide (75 mL). The mixture was stirred for <30 seconds before the addition of neopentylamine (1.85 mL of 300 mM in DMF, 48.4 mg, 0.555 mmol, 1 equiv.). The reaction vessel was wrapped in aluminum foil to prevent exposure to light. After 15-20 mins, the reactions started to change from the initial clear and colorless solution to a light orange color that continues to intensify as the reaction proceeds. IR was used to monitor the reaction progression via disappearance of the Sar NCA carbonyl stretches at ~1850 and 1778 cm$^{-1}$, with the latter being the preferred wavenumber to monitor. The next day, after a total of 22 h the reaction was complete. The circulating bath temperature was increased to 25° C. prior to the addition of D-phenylalanine N-carboxyanhydride (1.06 g, 5.55 mmol, 10 equiv.) and L-tyrosine N-carboxyanhydride (3.45 g, 16.7 mmol, 30 equiv.). Additional DMF (~5 mL) was used to rinse down the sides of the funnel and reaction vessel. Significant $CO_2$ gas formation was observed shortly after the reaction was initiated. IR was used to monitor the reaction progression via disappearance of the D-Phe NCA and L-Tyr NCA carbonyl stretches at ~1847 and 1786 cm$^{-1}$, with the latter being the preferred wavenumber to monitor. As the reaction proceeds, the color changed from a clear bright orange to a clear yellow-orange solution that was apparent after only a few hours. The reaction was complete after a total of 30 h. The reaction mixture (total of ~100 mL) was transferred to a beaker and fitted with an overhead stirrer. While vigorously stirring, ethyl acetate (400 mL, 4 volumes) was added to precipitate the product. The solids were collected via filtration into a medium fritted glass funnel, and then the semi-dry material was transferred back to the original precipitation beaker along with additional EtOAc (200 mL, 2 volumes) and slurried with vigorous stirring for 20 mins. The solids were collected in the same glass funnel and washed with additional EtOAc (100 mL, 1 volume) once more. The product was dried in a vacuum oven at 90-100° C. for 2 days to yield 11.3 g (87.9%) of the title compound as a fine off-white powder. $^1$H NMR (DMSO-d$_6$) δ 9.3-9.0 (28H), 8.5-7.8 (45H), 7.4-6.4 (170H), 4.6-3.6 (784H), 3.2-2.5 (1326H), 1.9 (5H), 1.2-1.1 (6H), 0.9-0.8 (14H); GPC (DMF, 50 mM LiBr) Mn=18.1 kDa, Mp=19.3 kDa, PDI=1.07.

Example 20—Preparation of Sar$_{235}$-b-p-[D-Phe$_{15}$-co-L-Tyr$_{25}$]

Following the general procedure of Example 19 with the following reagent equivalents and amounts: neopentylamine (16.1 mg, 1 equiv.), sarcosine NCA (5.0 g, 235 equiv.), D-Phe NCA (0.531 g, 15 equiv.), and L-Tyr (0.959 g, 25 equiv.). This yielded the title compound as a cream colored solid (3.24 g, 75.9%). GPC (DMF, 50 mM LiBr) Mn=17.1 kDa, Mp=18.2 kDa, PDI=1.07.

Example 21—Preparation of Sar$_{235}$-b-p-[D-Phe$_{5}$-co-L-Tyr$_{35}$]

Following the general procedure of Example 19 with the following reagent equivalents and amounts: neopentylamine (16.1 mg, 1 equiv.), sarcosine NCA (5.0 g, 235 equiv.), D-Phe NCA (0.177 g, 5 equiv.), and L-Tyr (1.34 g, 35 equiv.). This yielded the title compound as a cream colored solid (3.89 g, 90.5%). GPC (DMF, 50 mM LiBr) Mn=17.0 kDa, Mp=18.1 kDa, PDI=1.10.

Example 22-30% Paclitaxel Feed with TFS-2

2.0 g of TFS-2 (poly(Sar)$_{175}$-block-poly(d-Leu$_{30}$-co-Tyr$_{20}$)) and 2.0 g of trehalose were dissolved in 90 mL of 30:70 (v/v) tert-butanol:water to produce a solution of 22.2 mg/mL of each component. The pH of the resulting solution was adjusted to pH 7.0 using 25 mM NaOH. Separately, paclitaxel (603 mg) was dissolved in 30 mL of tert-butanol with the assistance of a sonicating water bath, to produce a solution of 20.1 mg/mL. The two solutions were mixed and stirred for 15 minutes before filtering through a 0.22 μm PVDF filter. The formulation solution was then transferred to 20 mL vials in 10 mL aliquots per vial, frozen at −80° C., and then lyophilized for 2 days. This yielded 4.2 g of a fragmented white cake containing paclitaxel at a weight loading of 12.9%.

Example 23—15% Paclitaxel Feed with TFS-2

100 mg of TFS-2 (poly(Sar)$_{175}$-block-poly(d-Leu$_{30}$-co-Tyr$_{20}$)) and 100 mg of trehalose were dissolved in 10 mL of 40:60 (v/v) tert-butanol:water to produce a solution of 10 mg/mL of each component. The pH of the resulting solution was adjusted to pH 7.0 using 25 mM NaOH. Separately, paclitaxel (15 mg) was dissolved in 0.75 mL of tert-butanol with the assistance of a sonicating water bath, to produce a solution of 20 mg/mL. The two solutions were mixed and stirred for 15 minutes before filtering through a 0.22 µm PVDF filter. The formulation solution was frozen at −80° C., and then lyophilized for 2 days. This yielded the drug product as a fragmented white cake containing paclitaxel at a weight loading of 7.51%.

Example 24—15% Paclitaxel Feed with TFS-1

Using the general method of Example 23 with the following exception: the copolymer used was TFS-1 (poly(Sar)$_{175}$-block-poly(d-Leu$_{35}$-co-Tyr$_{25}$)). This yielded the drug product as a fragmented white cake containing paclitaxel at a weight loading of 6.90%.

Example 25—20% Paclitaxel Feed with TFS-2

Using the general method of Example 23 with the following exception: the drug solution consisted of 20 mg of paclitaxel dissolved in 1.0 mL of tert-butanol. This yielded the drug product as a fragmented white cake containing paclitaxel at a weight loading of 9.33%.

Example 26—20% Paclitaxel Feed with TFS-1

Using the general method of Example 23 with the following exceptions: the copolymer used was TFS-1 (poly(Sar)$_{175}$-block-poly(d-Leu$_{35}$-co-Tyr$_{25}$)); and the drug solution consisted of 20 mg of paclitaxel dissolved in 1.0 mL of tert-butanol. This yielded the drug product as a fragmented white cake containing paclitaxel at a weight loading of 9.20%.

Example 27—25% Paclitaxel Feed with TFS-2

50 mg of TFS-2 (poly(Sar)$_{175}$-block-poly(d-Leu$_{30}$-co-Tyr$_{20}$)) and 50 mg of trehalose were dissolved in 5 mL of 40:60 (v/v) tert-butanol:water to produce a solution of 10 mg/mL of each component. The pH of the resulting solution was adjusted to pH 7.0 using 25 mM NaOH. Separately, paclitaxel (12.5 mg) was dissolved in 0.625 mL of tert-butanol with the assistance of a sonicating water bath, to produce a solution of 20 mg/mL. The two solutions were mixed and stirred for 15 minutes before filtering through a 0.22 µm PVDF filter. The formulation solution was frozen at −80° C., and then lyophilized for 2 days. This yielded the drug product as a fragmented white cake containing paclitaxel at a weight loading of 11.4%.

Example 28—30% Paclitaxel Feed with TFS-2

Using the general method of Example 27 with the following exception: the drug solution consisted of 15 mg of paclitaxel dissolved in 0.75 mL of tert-butanol. This yielded the drug product as a fragmented white cake containing paclitaxel at a weight loading of 14.6%.

Example 29—25% Paclitaxel Feed (at 4 mg/mL) with TFS-2

100 mg of TFS-2 (poly(Sar)$_{175}$-block-poly(d-Leu$_{30}$-co-Tyr$_{20}$)) and 100 mg of trehalose were dissolved in 5 mL of 35:65 (v/v) tert-butanol:water to produce a solution of 20 mg/mL of each component. The pH of the resulting solution was adjusted to pH 7.0 using 25 mM NaOH. Separately, paclitaxel (25 mg) was dissolved in 1.25 mL of tert-butanol with the assistance of a sonicating water bath, to produce a solution of 20 mg/mL. The two solutions were mixed and stirred for 15 minutes to produce a solution with a paclitaxel concentration of 4 mg/mL which was then filtering through a 0.22 µm PVDF filter. The formulation solution was frozen at −80° C., and then lyophilized for 2 days. This yielded the drug product as a fragmented white cake containing paclitaxel at a weight loading of 9.9%.

Example 30—30% Paclitaxel Feed (at 4 mg/mL) with TFS-2

Using the general method of Example 29 with the following exceptions: 100 mg of TFS-2 (poly(Sar)$_{175}$-block-poly(d-Leu$_{30}$-co-Tyr$_{20}$)) and 100 mg of trehalose were dissolved in 6 mL of 35:65 (v/v) tert-butanol:water to produce a solution of 16.7 mg/mL of each component; and the drug solution consisted of 30 mg of paclitaxel dissolved in 1.5 mL of tert-butanol. This yielded the drug product as a fragmented white cake containing paclitaxel at a weight loading of 11.7%.

Example 31—35% Paclitaxel Feed (at 4 mg/mL) with TFS-2

Using the general method of Example 29 with the following exceptions: 100 mg of TFS-2 (poly(Sar)$_{175}$-block-poly(d-Leu$_{30}$-co-Tyr$_{20}$)) and 100 mg of trehalose were dissolved in 7 mL of 35:65 (v/v) tert-butanol:water to produce a solution of 14.3 mg/mL of each component; and the drug solution consisted of 35 mg of paclitaxel dissolved in 1.75 mL of tert-butanol. This yielded the drug product as a fragmented white cake containing paclitaxel at a weight loading of 14.3%.

Example 32—25% Paclitaxel Feed (at 5 mg/mL) with TFS-2

100 mg of TFS-2 (poly(Sar)$_{175}$-block-poly(d-Leu$_{30}$-co-Tyr$_{20}$)) and 100 mg of trehalose were dissolved in 3.75 mL of 35:65 (v/v) tert-butanol:water to produce a solution of 26.7 mg/mL of each component. The pH of the resulting solution was adjusted to pH 7.0 using 25 mM NaOH. Separately, paclitaxel (25 mg) was dissolved in 1.25 mL of tert-butanol with the assistance of a sonicating water bath, to produce a solution of 20 mg/mL. The two solutions were mixed and stirred for 15 minutes to produce a solution with a paclitaxel concentration of 5 mg/mL which was then filtering through a 0.22 µm PVDF filter. The formulation solution was frozen at −80° C., and then lyophilized for 2 days. This yielded the drug product as a fragmented white cake containing paclitaxel at a weight loading of 10.2%

Example 33—30% Paclitaxel Feed (at 5 mg/mL) with TFS-2

Using the general method of Example 32 with the following exceptions: 100 mg of TFS-2 (poly(Sar)$_{175}$-block-poly(d-Leu$_{30}$-co-Tyr$_{20}$)) and 100 mg of trehalose were dissolved in 4.5 mL of 35:65 (v/v) tert-butanol:water to produce a solution of 22.2 mg/mL of each component; and the drug solution consisted of 30 mg of paclitaxel dissolved in 1.5 mL of tert-butanol. This yielded the drug product as a fragmented white cake containing paclitaxel at a weight loading of 11.5%.

Example 34—35% Paclitaxel Feed (at 5 mg/mL) with TFS-2

Using the general method of Example 32 with the following exceptions: 100 mg of TFS-2 (poly(Sar)$_{175}$-block-poly(d-Leu$_{30}$-co-Tyr$_{20}$)) and 100 mg of trehalose were dissolved in 5.25 mL of 35:65 (v/v) tert-butanol:water to produce a solution of 19.0 mg/mL of each component; and the drug solution consisted of 35 mg of paclitaxel dissolved in 1.75 mL of tert-butanol. This yielded the drug product as a fragmented white cake containing paclitaxel at a weight loading of 13.1%.

Example 35—2.5% Paclitaxel Feed with Sar$_{125}$-b-p-[D-Glu(OBn)$_{15}$-co-L-Glu(OBn)$_{15}$] and No Cryoprotectant 200 mg of poly(Sar)$_{125}$-block-poly[(d-Glu(OBn)$_{15}$-co-L-Glu(OBn)$_{15}$] was dissolved in 10 mL of 40:60 (v/v) tert-butanol:water to produce a solution of 20 mg/mL of the polymer. Separately, paclitaxel (5 mg) was dissolved in 0.25 mL of tert-butanol with the assistance of a sonicating water bath, to produce a solution of 20 mg/mL. The two solutions were mixed and stirred for 15 minutes and then filtering through a 0.22 µm PVDF filter. The formulation solution was frozen at −80° C., and then lyophilized for 2 days. This yielded the drug product as a white solid containing paclitaxel at a weight loading of 3.0%

Example 36—5.0% Paclitaxel Feed with Sar$_{125}$-b-p-[D-Glu(OBn)$_{15}$-co-L-Glu(OBn)$_{15}$] and No Cryoprotectant Using the general method of Example 35 with the following exceptions: the drug substance solution consisted of 10 mg of paclitaxel dissolved in 0.5 mL of tert-butanol which was added to the polymer solution. This yielded the drug product as a white solid containing paclitaxel at a weight loading of 6.3%.

Example 37—10.0% Paclitaxel Feed with Sar$_{125}$-b-p-[D-Glu(OBn)$_{15}$-co-L-Glu(OBn)$_{15}$] and No Cryoprotectant Using the general method of Example 35 with the following exceptions: the drug substance solution consisted of 20 mg of paclitaxel dissolved in 1.0 mL of tert-butanol which was added to the polymer solution. This yielded the drug product as a white solid containing paclitaxel at a weight loading of 11.1%.

Example 38—2.5% Paclitaxel Feed with Sar$_{125}$-b-p-[D-Glu(OBn)$_{15}$-co-L-Glu(OBn)$_{15}$]

100 mg of poly(Sar)$_{125}$-block-poly[d-Glu(OBn)$_{15}$-co-L-Glu(OBn)$_{15}$] and 100 mg of trehalose was dissolved in 5 mL of 40:60 (v/v) tert-butanol:water to produce a solution of 20 mg/mL of each component. Separately, paclitaxel (2.5 mg) was dissolved in 0.125 mL of tert-butanol with the assistance of a sonicating water bath, to produce a solution of 20 mg/mL. The two solutions were mixed and stirred for 15 minutes and then filtering through a 0.22 µm PVDF filter. The formulation solution was frozen at −80° C., and then lyophilized for 2 days. This yielded the drug product as a fragmented white cake containing paclitaxel at a weight loading of 1.6%

Example 39—5% Paclitaxel Feed with Sar$_{125}$-b-p-[D-Glu(OBn)$_{15}$-co-L-Glu(OBn)$_{15}$]

Using the general method of Example 38 with the following exceptions: the drug substance solution consisted of 5.0 mg of paclitaxel dissolved in 0.25 mL of tert-butanol which was added to the polymer and trehalose solution. This yielded the drug product as a white solid containing paclitaxel at a weight loading of 1.9%.

Example 40—10% Paclitaxel Feed with Sar$_{125}$-b-p-[D-Glu(OBn)$_{15}$-co-L-Glu(OBn)$_{15}$]

Using the general method of Example 38 with the following exceptions: the drug substance solution consisted of 10.0 mg of paclitaxel dissolved in 0.5 mL of tert-butanol which was added to the polymer and trehalose solution. This yielded the drug product as a white solid containing paclitaxel at a weight loading of 4.1%.

Example 41—2.5% Paclitaxel Feed with Sar$_{125}$-b-p-[D-Glu(OBn)$_{20}$-co-L-Glu(OBn)$_{20}$] and No Cryoprotectant 200 mg of poly(Sar)$_{125}$-block-poly[d-Glu(OBn)$_{20}$-co-L-Glu(OBn)$_{20}$] was dissolved in 10 mL of 40:60 (v/v) tert-butanol:water to produce a solution of 20 mg/mL of the polymer. Separately, paclitaxel (5 mg) was dissolved in 0.25 mL of tert-butanol with the assistance of a sonicating water bath, to produce a solution of 20 mg/mL. The two solutions were mixed and stirred for 15 minutes and then filtering through a 0.22 µm PVDF filter. The formulation solution was frozen at −80° C., and then lyophilized for 2 days. This yielded the drug product as a white solid containing paclitaxel at a weight loading of 2.7%

Example 42—5.0% Paclitaxel Feed with Sar$_{125}$-b-p-[D-Glu(OBn)$_{20}$-co-L-Glu(OBn)$_{20}$] and No Cryoprotectant Using the general method of Example 41 with the following exceptions: the drug substance solution consisted of 10 mg of paclitaxel dissolved in 0.5 mL of tert-butanol which was added to the polymer solution. This yielded the drug product as a white solid containing paclitaxel at a weight loading of 5.1%.

Example 43—10.0% Paclitaxel Feed with Sar$_{125}$-b-p-[D-Glu(OBn)$_{20}$-co-L-Glu(OBn)$_{20}$] and No Cryoprotectant Using the general method of Example 41 with the following exceptions: the drug substance solution consisted of 20 mg of paclitaxel dissolved in 1.0 mL of tert-butanol which was added to the polymer solution. This yielded the drug product as a white solid containing paclitaxel at a weight loading of 8.3%.

Example 44—2.5% Paclitaxel Feed with Sar$_{125}$-b-p-[D-Glu(OBn)$_{20}$-co-L-Glu(OBn)$_{20}$]

100 mg of poly(Sar)$_{125}$-block-poly[d-Glu(OBn)$_{20}$-co-L-Glu(OBn)$_{20}$] and 100 mg of trehalose was dissolved in 5 mL of 40:60 (v/v) tert-butanol:water to produce a solution of 20 mg/mL of each component. Separately, paclitaxel (2.5 mg) was dissolved in 0.125 mL of tert-butanol with the assistance of a sonicating water bath, to produce a solution of 20 mg/mL. The two solutions were mixed and stirred for 15 minutes and then filtering through a 0.22 µm PVDF filter. The formulation solution was frozen at −80° C., and then lyophilized for 2 days. This yielded the drug product as a fragmented white cake containing paclitaxel at a weight loading of 1.4%

Example 45—5% Paclitaxel Feed with $Sar_{125}$-b-p-[D-Glu(OBn)$_{20}$-co-L-Glu(OBn)$_{20}$]

Using the general method of Example 44 with the following exceptions: the drug substance solution consisted of 5.0 mg of paclitaxel dissolved in 0.25 mL of tert-butanol which was added to the polymer and trehalose solution. This yielded the drug product as a white solid containing paclitaxel at a weight loading of 2.5%.

Example 46—10% Paclitaxel Feed with $Sar_{125}$-b-p-[D-Glu(OBn)$_{20}$-co-L-Glu(OBn)$_{20}$]

Using the general method of Example 44 with the following exceptions: the drug substance solution consisted of 10.0 mg of paclitaxel dissolved in 0.5 mL of tert-butanol which was added to the polymer and trehalose solution. This yielded the drug product as a white solid containing paclitaxel at a weight loading of 4.3%.

Example 47—15% SN-38 Feed with TFS-3

Trehalose (8.0 g) was dissolved in 400 mL of water before the addition of 2.0 g of TFS-3 ($Sar_{235}$[D-Phe$_{10}$-co-Tyr$_{30}$]) to produce a solution of 20 mg/mL trehalose and 5 mg/mL TFS-3. The resulting solution was stirred for 1 hour before filtering through a 0.5 µm polypropylene filter. Separately, a solution of SN-38 was prepared by dissolving 281 mg in 3.75 mL of DMSO, with the assistance of heat, to produce a stock solution of 75 mg/mL. While shear mixing 375 mL of the polymer/trehalose solution with a homogenizer at 10,000 RPM, the SN-38 stock solution was added, and the mixing was continued for 1 minute. The resulting homogenous emulsion was processed with two passes through a microfluidizer with an inlet pressure of 100 PSI and an operating pressure of approximately 25,000 PSI through an auxiliary processing chamber followed by a 50 µm X interaction chamber with the outlet tube cooled in an ice-water bath. The extruded solution was then diafiltered against 2.5 L of 20 mg/mL trehalose using a tangential flow filtration system equipped with a mPES hollow fiber filter (10 kDa MWCO, 790 cm$^2$ surface area) at a flow rate of 300 mL/min. The solution was then concentrated to ~¼ the original volume such that the final polymer concentration was ~20 mg/mL. The formulation solution was then filtered through a 0.2 µm PES filter with a surface area of 20 cm$^2$. The filtered solution was frozen at −80° C. and lyophilized for 2 days. This yielded the drug formulation as a fragmented, slightly yellow cake with an SN-38 weight loading of 5.73%.

Example 48—20% SN-38 Feed with TFS-3

Using the general method of Example 47 with the following exception: a total of 5.0 mL of the SN-38 solution (75 mg/mL) was homogenized with 375 mL of the polymer/trehalose solution. This yielded the drug product as a fragmented, slightly yellow cake with an SN-38 weight loading of 7.54%

Example 49—25% SN-38 Feed with TFS-3

Using the general method of Example 47 with the following exception: a total of 6.25 mL of the SN-38 solution (75 mg/mL) was homogenized with 375 mL of the polymer/trehalose solution. This yielded the drug product as a fragmented, slightly yellow cake with an SN-38 weight loading of 9.35%

Example 50-30% SN-38 Feed with TFS-3

Using the general method of Example 47 with the following exception: a total of 7.5 mL of the SN-38 solution (75 mg/mL) was homogenized with 375 mL of the polymer/trehalose solution. This yielded the drug product as a fragmented, slightly yellow cake with an SN-38 weight loading of 11.64%.

Example 51—40% SN-38 Feed with TFS-3

Using the general method of Example 47 with the following exception: a total of 10.0 mL of the SN-38 solution (75 mg/mL) was homogenized with 375 mL of the polymer/trehalose solution. This yielded the drug product as a fragmented, yellow cake with an SN-38 weight loading of 14.80%

Example 52—10% SN-38 Feed with $Sar_{175}$-b-p-[D-Phe$_{25}$-co-L-Glu(OBn)$_{25}$]

Trehalose (750 mg) was dissolved in 150 mL of water before the addition of 750 mg of $Sar_{175}$-b-p-[D-Phe$_{25}$-co-L-Glu(OBn)$_{25}$] to produce a solution of 5 mg/mL of each component. Separately, a solution of SN-38 was prepared by dissolving 75 mg in 1.0 mL of DMSO, with the assistance of heat, to produce a stock solution of 75 mg/mL. While shear mixing the polymer/trehalose solution with a homogenizer at 10,000 RPM, the SN-38 stock solution was added, and the mixing was continued for 1 minute. The resulting homogenous emulsion was processed through a microfluidizer with an inlet pressure of 100 PSI and an operating pressure of approximately 25,000 PSI through an auxiliary processing chamber followed by a 50 µm X interaction chamber with the outlet tube cooled in an ice-water bath. The extruded solution was then diafiltered against 1.2 L of 5 mg/mL trehalose using a tangential flow filtration system equipped with a mPES hollow fiber filter (10 kDa MWCO, 790 cm$^2$ surface area) at a flow rate of 300 mL/min. Half of the formulation solution was frozen at −80° C. and lyophilized for 2 days. The other half of the formulation was filtered through a 0.2 µm PES filter, frozen at −80° C. and lyophilized for 2 days. This yielded the drug formulations as a fragmented, slightly yellow cakes with an SN-38 weight loading of 2.8% for the unfiltered formulation and 0.3% for the filtered formulation.

Example 53—10% SN-38 Feed with $Sar_{175}$-b-p-[D-Phe$_{10}$-co-L-Tyr$_{30}$]

Using the general method of Example 52 with the following exception: the polymer used was $Sar_{175}$-b-p-[D-Phe$_{10}$-co-L-Tyr$_{30}$]. This yielded the drug formulations as a fragmented, slightly yellow cakes with an SN-38 weight loading of 4.2% for the unfiltered formulation and 4.1% for the filtered formulation.

Example 54—10% SN-38 Feed with $Sar_{175}$-b-p-[D-$Phe_{25}$-co-L-$Tyr_{15}$]

Using the general method of Example 52 with the following exception: the polymer used was $Sar_{175}$-b-p-[D-$Phe_{25}$-co-L-$Tyr_{15}$]. This yielded the drug formulations as a fragmented, slightly yellow cakes with an SN-38 weight loading of 4.1% for the unfiltered formulation and 0.5% for the filtered formulation.

Example 55—10% SN-38 Feed with $Sar_{175}$-b-p-[D-$Phe_{15}$-co-L-$Tyr_{25}$]

Using the general method of Example 52 with the following exception: the polymer used was $Sar_{175}$-b-p-[D-$Phe_{15}$-co-L-$Tyr_{25}$]. This yielded the drug formulations as a fragmented, slightly yellow cakes with an SN-38 weight loading of 3.9% for the unfiltered formulation and 2.8% for the filtered formulation.

Example 56—15% SN-38 Feed with $Sar_{210}$-b-p-[D-$Phe_{15}$-co-L-$Tyr_{25}$]

Trehalose (1.0 g) was dissolved in 200 mL of water before the addition of 1.0 g of $Sar_{210}$-b-p-[D-$Phe_{15}$-co-L-$Tyr_{25}$] to produce a solution of 5 mg/mL of each component. Separately, a solution of SN-38 was prepared by dissolving 150 mg in 2.0 mL of DMSO, with the assistance of heat, to produce a stock solution of 75 mg/mL. While shear mixing the polymer/trehalose solution with a homogenizer at 10,000 RPM, the SN-38 stock solution was added, and the mixing was continued for 1 minute. The resulting homogenous emulsion was processed through a microfluidizer with an inlet pressure of 100 PSI and an operating pressure of approximately 25,000 PSI through an auxiliary processing chamber followed by a 50 μm X interaction chamber with the outlet tube cooled in an ice-water bath. Approximately 120 mL of the extruded solution was then diafiltered against 600 mL of 5 mg/mL trehalose using a tangential flow filtration system equipped with a mPES hollow fiber filter (10 kDa MWCO, 790 $cm^2$ surface area) at a flow rate of 300 mL/min. The formulation was filtered through a 0.45 μm PVDF filter and then through a 0.2 PES μm filter, frozen at −80° C. and lyophilized for 2 days. This yielded the drug formulation as a fragmented, slightly yellow cake with an SN-38 weight loading of 5.0%.

Example 57—15% SN-38 Feed with $Sar_{175}$-b-p-[D-$Phe_{10}$-co-L-$Tyr_{30}$]

Using the general method of Example 56 with the following exception: the polymer used was $Sar_{175}$-b-p-[D-$Phe_{10}$-co-L-$Tyr_{30}$]. This yielded the drug formulation as a fragmented, slightly yellow cake with an SN-38 weight loading of 4.9%.

Example 58—15% SN-38 Feed with $Sar_{175}$-b-p-[D-$Phe_{5}$-co-L-$Tyr_{35}$]

Using the general method of Example 56 with the following exception: the polymer used was $Sar_{175}$-b-p-[D-$Phe_{5}$-co-L-$Tyr_{35}$]. This yielded the drug formulation as a fragmented, slightly yellow cake with an SN-38 weight loading of 2.9%.

Example 59—10% SN-38 Feed with $Sar_{210}$-b-p-[D-$Phe_{15}$-co-L-$Tyr_{25}$]

Trehalose (1.0 g) was dissolved in 200 mL of water before the addition of 1.0 g of $Sar_{210}$-b-p-[D-$Phe_{15}$-co-L-$Tyr_{25}$] to produce a solution of 5 mg/mL of each component. The polymer/trehalose solution was heated to 65° C. for ~30 mins to assist in dissolution. Separately, a solution of SN-38 was prepared by dissolving 100 mg in 1.33 mL of DMSO, with the assistance of heat, to produce a stock solution of 75 mg/mL. While shear mixing the polymer/trehalose solution with a homogenizer at 10,000 RPM, the SN-38 stock solution was added, and the mixing was continued for 1 minute. The resulting homogenous emulsion was processed through a microfluidizer with an inlet pressure of 100 PSI and an operating pressure of approximately 25,000 PSI through an auxiliary processing chamber followed by a 50 μm X interaction chamber with the outlet tube cooled in an ice-water bath. Approximately 120 mL of the extruded solution was then diafiltered against 600 mL of 5 mg/mL trehalose using a tangential flow filtration system equipped with a mPES hollow fiber filter (10 kDa MWCO, 790 $cm^2$ surface area) at a flow rate of 300 mL/min. The formulation was filtered through a 0.45 μm PVDF filter and then through a 0.2 μm PES filter, frozen at −80° C. and lyophilized for 2 days. This yielded the drug formulation as a fragmented, slightly yellow cake with an SN-38 weight loading of 3.8%.

Example 60—10% SN-38 Feed with $Sar_{210}$-b-p-[D-$Phe_{10}$-co-L-$Tyr_{30}$]

Using the general method of Example 59 with the following exception: the polymer used was $Sar_{210}$-b-p-[D-$Phe_{10}$-co-L-$Tyr_{30}$]. This yielded the drug formulation as a fragmented, slightly yellow cake with an SN-38 weight loading of 3.4%.

Example 61—15% SN-38 Feed with $Sar_{210}$-b-p-[D-$Phe_{15}$-co-L-$Tyr_{25}$]

Trehalose (1.0 g) was dissolved in 200 mL of water before the addition of 1.0 g of $Sar_{210}$-b-p-[D-$Phe_{15}$-co-L-$Tyr_{25}$] to produce a solution of 5 mg/mL of each component. The polymer/trehalose solution was stirred overnight to assist in dissolution and then filtered through a 0.2 μm PES filter. Separately, a solution of SN-38 was prepared by dissolving 150 mg in 2.0 mL of DMSO, with the assistance of heat, to produce a stock solution of 75 mg/mL. While shear mixing the polymer/trehalose solution with a homogenizer at 10,000 RPM, the SN-38 stock solution was added, and the mixing was continued for 1 minute. The resulting homogenous emulsion was processed through a microfluidizer with an inlet pressure of 100 PSI and an operating pressure of approximately 25,000 PSI through an auxiliary processing chamber followed by a 50 μm X interaction chamber with the outlet tube cooled in an ice-water bath. Approximately 120 mL of the extruded solution was then diafiltered against 600 mL of 5 mg/mL trehalose using a tangential flow filtration system equipped with a mPES hollow fiber filter (10 kDa MWCO, 790 $cm^2$ surface area) at a flow rate of 300 mL/min. The formulation was filtered through a 0.45 μm PVDF filter and then through a 0.2 μm PES filter, frozen at −80° C. and lyophilized for 2 days. This yielded the drug formulation as a fragmented, slightly yellow cake with an SN-38 weight loading of 1.4%.

Example 62—15% SN-38 Feed with $Sar_{210}$-b-p-[D-$Phe_{10}$-co-L-$Tyr_{30}$]

Using the general method of Example 61 with the following exception: the polymer used was $Sar_{210}$-b-p-[D-$Phe_{10}$-co-L-$Tyr_{30}$]. This yielded the drug formulation as a fragmented, slightly yellow cake with an SN-38 weight loading of 3.0%.

Example 63—15% SN-38 Feed with $Sar_{235}$-b-p-[D-$Phe_{15}$-co-L-$Tyr_{25}$]

Using the general method of Example 61 with the following exception: the polymer used was $Sar_{235}$-b-p-[D-$Phe_{15}$-co-L-$Tyr_{25}$]. This yielded the drug formulation as a fragmented, slightly yellow cake with an SN-38 weight loading of 1.6%.

Example 64—15% SN-38 Feed with TFS-3 ($Sar_{235}$-b-p-[D-$Phe_{10}$-co-L-$Tyr_{30}$])

Using the general method of Example 61 with the following exception: the polymer used was TFS-3 ($Sar_{235}$-b-p-[D-$Phe_{10}$-co-L-$Tyr_{30}$]). This yielded the drug formulation as a fragmented, slightly yellow cake with an SN-38 weight loading of 3.7%.

Example 65—6% SN-38 Feed with $Sar_{235}$-b-p-[D-$Phe_{15}$-co-L-$Tyr_{25}$]

Trehalose (1.0 g) was dissolved in 200 mL of water before the addition of 1.0 g of $Sar_{235}$-b-p-[D-$Phe_{15}$-co-L-$Tyr_{25}$] to produce a solution of 5 mg/mL of each component. The polymer/trehalose solution was stirred overnight to assist in dissolution and then filtered through a 0.8/0.45 μm PES filter. Separately, a solution of SN-38 was prepared by dissolving 45 mg in 0.6 mL of DMSO, with the assistance of heat, to produce a stock solution of 75 mg/mL. While shear mixing 150 mL of the filtered polymer/trehalose solution with a homogenizer at 10,000 RPM, the SN-38 stock solution was added, and the mixing was continued for 1 minute. The resulting homogenous emulsion was processed through a microfluidizer with an inlet pressure of 100 PSI and an operating pressure of approximately 25,000 PSI through an auxiliary processing chamber followed by a 50 μm X interaction chamber with the outlet tube cooled in an ice-water bath. Approximately 120 mL of the extruded solution was then diafiltered against 600 mL of 5 mg/mL trehalose using a tangential flow filtration system equipped with a mPES hollow fiber filter (10 kDa MWCO, 790 cm$^2$ surface area) at a flow rate of 300 mL/min. The formulation was filtered through a 0.45 μm PVDF filter and then through a 0.2 μm PES filter, frozen at −80° C. and lyophilized for 2 days. This yielded the drug formulation as a fragmented, slightly yellow cake with an SN-38 weight loading of 2.02%.

Example 66—8% SN-38 Feed with $Sar_{235}$-b-p-[D-$Phe_{15}$-co-L-$Tyr_{25}$]

Using the general method of Example 65 with the following exception: the SN-38 solution consisted of 60 mg dissolved in 0.8 mL of DMSO. This yielded the drug formulation as a fragmented, slightly yellow cake with an SN-38 weight loading of 2.49%.

Example 67—6% SN-38 Feed with TFS-3 ($Sar_{235}$-b-p-[D-$Phe_{10}$-co-L-$Tyr_{30}$])

Using the general method of Example 65 with the following exception: the polymer used was TFS-3 ($Sar_{235}$-b-p-[D-$Phe_{10}$-co-L-$Tyr_{30}$]). This yielded the drug formulation as a fragmented, slightly yellow cake with an SN-38 weight loading of 2.35%.

Example 68—8% SN-38 Feed with TFS-3 ($Sar_{235}$-b-p-[D-$Phe_{10}$-co-L-$Tyr_{30}$])

Using the general method of Example 65 with the following exceptions: the polymer used was TFS-3 ($Sar_{235}$-b-p-[D-$Phe_{10}$-co-L-$Tyr_{30}$]), and the SN-38 solution consisted of 60 mg dissolved in 0.8 mL of DMSO. This yielded the drug formulation as a fragmented, slightly yellow cake with an SN-38 weight loading of 2.88%.

Example 69—15% Cabazitaxel Feed with ($Sar_{125}$-b-p-[D-$Leu_{20}$-co-L-$Tyr_{15}$])

100 mg of poly($Sar$)$_{125}$-block-poly(d-$Leu_{20}$-co-$Tyr_{15}$) and 100 mg of trehalose were dissolved in 10 mL of 40:60 (v/v) tert-butanol:water to produce a solution of 10 mg/mL of each component. Separately, cabazitaxel (15 mg) was dissolved in 1.65 mL of 13% (v/v) DMSO in tert-butanol with the assistance of a sonicating water bath, to produce a solution of 9 mg/mL. The two solutions were mixed and stirred for 15 minutes then filtering through a 0.22 μm PVDF filter. The formulation solution was frozen at −80° C., and then lyophilized for 2 days. This yielded the drug product as a fragmented white cake containing cabazitaxel at a weight loading of 1.82%

Example 70—15% Cabazitaxel Feed with ($Sar_{175}$-b-p-[D-$Glu(OBn)_{25}$-co-L-$Glu(OBn)_{15}$])

Using the general method of Example 69 with the following exception: the polymer used was poly($Sar$)$_{175}$-block-poly(d-$Glu(OBn)_{25}$-co-L-$Glu(OBn)_{25}$). This yielded the drug product as a fragmented white cake containing cabazitaxel at a weight loading of 2.22%

Example 71—15% Cabazitaxel Feed with TFS-2 ($Sar_{175}$-b-p-[D-$Leu_{30}$-co-L-$Tyr_{20}$])

Using the general method of Example 69 with the following exception: the polymer used was TFS-2 (poly($Sar$)$_{175}$-block-poly(D-$Leu_{30}$-co-L-$Tyr_{20}$)). This yielded the drug product as a fragmented white cake containing cabazitaxel at a weight loading of 2.00%

Example 72—15% Cabazitaxel Feed with TFS-1 ($Sar_{175}$-b-p-[D-$Leu_{35}$-co-L-$Tyr_{25}$])

Using the general method of Example 69 with the following exceptions: the polymer used was TFS-1 (poly($Sar$)$_{175}$-block-poly(D-$Leu_{35}$-co-L-$Tyr_{25}$)). This yielded the drug product as a fragmented white cake containing cabazitaxel at a weight loading of 1.84%

Example 73—10% Cabazitaxel Feed with TFS-2 ($Sar_{175}$-b-p-[D-$Leu_{30}$-co-L-$Tyr_{20}$])

200 mg of TFS-2 (poly($Sar$)$_{175}$-block-poly(d-$Leu_{30}$-co-$Tyr_{20}$)) as placed in a beaker equipped with a magnetic stir bar and dissolved in 100 mL of DI water. Separately, cabazitaxel (20 mg) was dissolved in 2 mL of dichloromethane. The aqueous solution was stirred vigorously, and the organic phase added drowse over approximately 1 minute. The solution was stirred overnight to allow the evaporation of dichloromethane. The resulting solution was vacuum filtered through a µm PVDF filter, frozen at −80° C., and then lyophilized for 2 days. This yielded the drug product as a fragmented white cake containing cabazitaxel at a weight loading of 0.77%

Example 74-10% Cabazitaxel Feed with TFS-1 (Sar$_{175}$-b-p-[D-Leu$_{35}$-co-L-Tyr$_{25}$])

Using the general method of Example 73 with the following exceptions: the polymer used was TFS-1 (poly(Sar)$_{175}$-block-poly(D-Leu$_{35}$-co-L-Tyr$_{25}$)). This yielded the drug product as a fragmented white cake containing cabazitaxel at a weight loading of 1.04%

Example 75—5% Docetaxel Feed with (Sar$_{125}$-b-p-[D-Leu$_{20}$-co-L-Tyr$_{15}$])

100 mg of poly(Sar)$_{125}$-block-poly(d-Leu$_{20}$-co-Tyr$_{15}$) and 100 mg of trehalose were dissolved in 10 mL of 40:60 (v/v) tert-butanol:water to produce a solution of 10 mg/mL of each component. Separately, docetaxel (5 mg) was dissolved in 0.25 mL of tert-butanol with the assistance of a sonicating water bath, to produce a solution of 20 mg/mL. The two solutions were mixed and stirred for 15 minutes, frozen at −80° C., and then lyophilized for 2 days. This yielded the drug product as a fragmented white cake containing docetaxel at a weight loading of 2.36%

Example 76—10% Docetaxel Feed with (Sar$_{125}$-b-p-[D-Leu$_{20}$-co-L-Tyr$_{15}$])

Using the general method of Example 75 with the following exception: the drug solution was prepared by dissolving docetaxel (10 mg) in 0.5 mL of tert-butanol. This yielded the drug product as a fragmented white cake containing docetaxel at a weight loading of 4.76%

Example 77—15% Docetaxel Feed with (Sar$_{125}$-b-p-[D-Leu$_{20}$-co-L-Tyr$_{15}$])

Using the general method of Example 75 with the following exception: the drug solution was prepared by dissolving docetaxel (10 mg) in 0.5 mL of tert-butanol. This yielded the drug product as a fragmented white cake containing docetaxel at a weight loading of 6.98%

The invention claimed is:

1. A method of increasing the solubility of a hydrophobic molecule in an aqueous solution comprising encapsulating the hydrophobic molecule in a multiblock copolymer of Formula I:

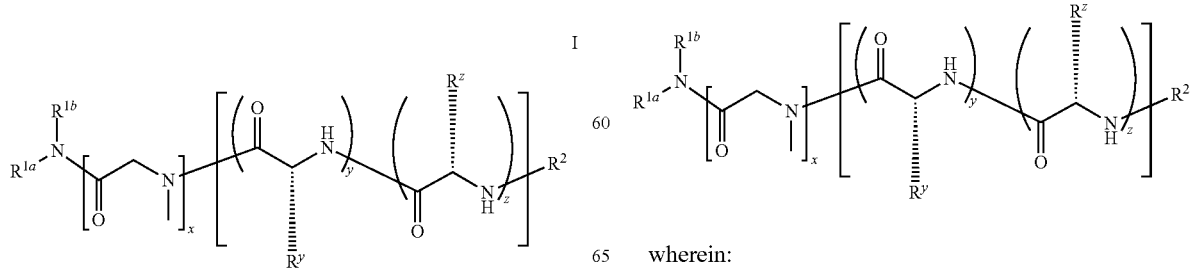

wherein:
$R^{1a}$ is H or an optionally substituted aliphatic group;
$R^{1b}$ is H or an optionally substituted aliphatic group;
$R^2$ is H, an optionally substituted aliphatic group or an optionally substituted CO—(C1-C6) aliphatic group;
each $R^y$ is independently the side chain of γ-benzyl-D-glutamate, D-leucine, D-tyrosine, D-phenylalanine, D-alanine, D-valine, D-isoleucine, D-norleucine, O-acetyl-D-tyrosine, O-benzyl-D-tyrosine, or ε-benzyl-D-lysine;
each $R^z$ is independently the side chain of γ-benzyl-L-glutamate, L-leucine, L-tyrosine, L-phenylalanine, L-alanine, L-valine, L-isoleucine, L-norleucine, O-acetyl-L-tyrosine, O-benzyl-L-tyrosine, or ε-benzyl-L-lysine;
x is 125-350;
y is 5-35;
z is 5-35.

2. The method according to claim 1, comprising:
a. providing the multiblock copolymer in an aqueous solution;
b. providing the hydrophobic molecule in an organic solution;
c. mixing the aqueous solution and the organic solution to produce an emulsion;
d. collecting a supernate from the emulsion;
e. producing a dry powder from the supernate; and
f. solubilizing the dry powder.

3. The method according to claim 2, wherein the aqueous solution and the organic solution are mixed with a homogenizer.

4. The method according to claim 2, wherein step d is replaced by the steps of processing the emulsion produced in step c using a microfluidizer to produce an extruded solution and filtering the extruded solution and collecting the supernate.

5. The method according to claim 2, wherein a cryoprotectant is added to the aqueous solution, the supernate or both.

6. The method according to claim 5, wherein the cryoprotectant is glycine, polyvinyl pyrrolidine, polyethylene glycol, mannitol, sorbitol, sucrose, glucose, raffinose, sucralose, lactose, trehalose, dextran, or dextrose.

7. The method according to claim 2, wherein the dry powder is produced via lyophilization.

8. The method according to claim 1, wherein the hydrophobic molecule is paclitaxel, docetaxel, cabazitaxel or SN-38, or a pharmaceutically acceptable salt of those compounds.

9. A method of preparing a composition comprising a multiblock copolymer of Formula I:

wherein:
$R^{1a}$ is H or an optionally substituted aliphatic group;
$R^{1b}$ is H or an optionally substituted aliphatic group;

$R^2$ is H, an optionally substituted aliphatic group or an optionally substituted CO—(C1-C6)aliphatic group;

each $R^y$ is independently the side chain of γ-benzyl-D-glutamate, D-leucine, D-tyrosine, D-phenylalanine, D-alanine, D-valine, D-isoleucine, D-norleucine, O-acetyl-D-tyrosine, O-benzyl-D-tyrosine, or ε-benzyl-D-lysine;

each $R^z$ is independently the side chain of γ-benzyl-L-glutamate, L-leucine, L-tyrosine, L-phenylalanine, L-alanine, L-valine, L-isoleucine, L-norleucine, O-acetyl-L-tyrosine, O-benzyl-L-tyrosine, or ε-benzyl-L-lysine;

x is 125-350;

y is 5-35; and z is 5-35, the method comprising dissolving a hydrophobic molecule, the copolymer of Formula I and, optionally, a cryoprotectant, in aqueous solution, to produce a mixed solution.

10. The method of claim 9, wherein the aqueous solution is tert-butanol and the method further comprises optionally lyophilizing the mixed solution.

11. The method of claim 9, wherein the method further comprises processing the mixed solution through a high shear mixer, to produce a high shear mixer solution, and optionally lyophilizing the high shear mixer solution.

12. A method of preparing a composition comprising a multiblock copolymer of Formula I:

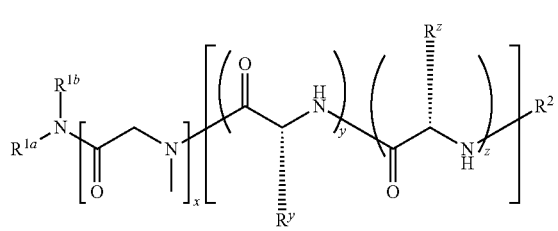

wherein:

$R^{1a}$ is H or an optionally substituted aliphatic group;

$R^{1b}$ is H or an optionally substituted aliphatic group;

$R^2$ is H, an optionally substituted aliphatic group or an optionally substituted CO—(C1-C6)aliphatic group;

each $R^y$ is independently the side chain of γ-benzyl-D-glutamate, D-leucine, D-tyrosine, D-phenylalanine, D-alanine, D-valine, D-isoleucine, D-norleucine, O-acetyl-D-tyrosine, O-benzyl-D-tyrosine, or ε-benzyl-D-lysine;

each $R^z$ is independently the side chain of γ-benzyl-L-glutamate, L-leucine, L-tyrosine, L-phenylalanine, L-alanine, L-valine, L-isoleucine, L-norleucine, O-acetyl-L-tyrosine, O-benzyl-L-tyrosine, or ε-benzyl-L-lysine;

x is 125-350;

y is 5-35; and z is 5-35, the method comprising:

a. dissolving a hydrophobic molecule in an organic solvent, to produce a hydrophobic molecule solution;

b. dissolving a copolymer of Formula I and, optionally, a cryoprotectant, in an aqueous solution, to produce a copolymer solution; and c. mixing the hydrophobic molecule solution and the copolymer solution to produce a mixed solution, and optionally lyophilizing the mixed solution.

13. The method of claim 12, wherein the hydrophobic molecule is paclitaxel and the hydrophobic molecule solution is a paclitaxel solution.

14. The method of claim 12, wherein the organic solvent is tert-butanol.

15. The method of claim 12, wherein the aqueous solution is a tert-butanol solution.

16. The method of claim 12, wherein the method further comprises filtering the mixed solution, to produce a filtered solution, and optionally lyophilizing the filtered solution.

17. The method of claim 12, wherein the method further comprises processing the mixed solution through a high shear mixer, to produce a high shear mixer solution, and optionally lyophilizing the high shear mixer solution.

18. The method of claim 17, wherein the method further comprises:

a. processing the high shear mixer solution with a diafiltration system, to produce a diafiltered solution;

b. filtering the diafiltered solution, to produce a filtered solution; and c. optionally lyophilizing the filtered solution.

* * * * *